US010766949B2

(12) United States Patent
Li et al.

(10) Patent No.: US 10,766,949 B2
(45) Date of Patent: Sep. 8, 2020

(54) METHOD FOR PREPARING WHOLE BOVINE-DERIVED BROADLY NEUTRALIZING ANTIBODY AGAINST SEROTYPE O FOOT-AND-MOUTH DISEASE VIRUS

(71) Applicant: Lanzhou Veterinary Research Institute, Chinese Academy of Agricultural Sciences, Lanzhou (CN)

(72) Inventors: Kun Li, Lanzhou (CN); Zengjun Lu, Lanzhou (CN); Zaixin Liu, Lanzhou (CN); Yimei Cao, Lanzhou (CN); Huifang Bao, Lanzhou (CN); Yingli Chen, Lanzhou (CN); Sheng Wang, Lanzhou (CN); Pinghua Li, Lanzhou (CN); Pu Sun, Lanzhou (CN); Xingwen Bai, Lanzhou (CN); Dong Li, Lanzhou (CN)

(73) Assignee: Lanzhour Veterinary Research Institute, Chinese Academy of Agricultural Sciences, Lanzhou (CN)

( * ) Notice: Subject to any disclaimer, the term of this patent is extended or adjusted under 35 U.S.C. 154(b) by 0 days.

(21) Appl. No.: 16/540,326

(22) Filed: Aug. 14, 2019

(65) Prior Publication Data
US 2020/0055925 A1    Feb. 20, 2020

(30) Foreign Application Priority Data

Aug. 15, 2018  (CN) .......................... 2018 1 0929067

(51) Int. Cl.
C07K 16/10    (2006.01)
(52) U.S. Cl.
CPC ...... C07K 16/1009 (2013.01); *C07K 2317/14* (2013.01); *C07K 2317/76* (2013.01)
(58) Field of Classification Search
None
See application file for complete search history.

(56) References Cited

U.S. PATENT DOCUMENTS

| 2015/0368352 A1* | 12/2015 | Liu | .................... | C07K 16/2803 530/387.3 |
| 2017/0216422 A1* | 8/2017 | Widener | .................. | C12N 7/00 |
| 2020/0055925 A1* | 2/2020 | Li | ..................... | C07K 16/1009 |

FOREIGN PATENT DOCUMENTS

| CN | 102533663 A | 7/2012 |
| CN | 102675471 A | 9/2012 |
| CN | 103007273 A | 4/2013 |
| CN | 103074349 A | 5/2013 |

OTHER PUBLICATIONS

Sok et al. (Nature. Aug. 2017; 548: 108-111).*
Yang et al. (Virus Research. 2011; 155: 291-299).*
McCullough and Butcher (Archives of Virology. 1982; 74: 1-9).*
Chinese Patent Office, Office Action and Search Report dated Mar. 15, 2019 (6 pages).
Chinese Patent Office, Notice of Allowance dated Apr. 25, 2019 (1 pages).
Harris, T. J. R., "Comparison of the Nucleotide Sequence at the 5' End of RNAs from Nine Aphthoviruses, Including Representatives of the Seven Serotypes," Journal of Virology (1980) 36(3):659-664.
Lu, L. et al., "Comparison of the full-length genomes of Mya98 lineage of type O foot-and-mouth disease viruses solated from pigs and cattle" (English language Abstract pp. 111-112), Chinese Veterinary Science (2014) 44(2):111-118.
Ma, Xueqing et al., "Genome sequence of foot-and-mouth disease virus outside the 3A region is also responsible for virus replication in bovine cells," Virus Research (2016) 220:64-69.
Nakamura, S. et al., "Impact of Sirolimus-Eluting Stent on the Outcome of Patients With Chronic Total Occlusions," Am. J. Cardiol. (2005) 95:161-166.
Yang, B. et al., "Cloning of structural protein VP1 gene of foot and mouth disease virus and its expression in *Escherichia coli*," (English language Abstract pp. 7-8), Chinese Journal of Veterinary Science and Technology (2003) 33(3):3-8.
Zhang, Y-G. et al., "Studies on Variations of 3A and VP1 Genes of Foot-and-mouth Disease Virus Strain O/China/99 from Serial Passages in Different Hosts" (English language Abstract p. 346), Chinese Journal of Virology (2004) 20(4):338-346.

* cited by examiner

*Primary Examiner* — Shanon A. Foley
(74) *Attorney, Agent, or Firm* — Wood Herron & Evans LLP

(57) ABSTRACT

The present invention relates to a method for preparing a whole bovine-derived broadly neutralizing antibody against serotype O foot-and-mouth disease virus, and belongs to the technical field of antibody preparation. The method includes the following steps: 1) conducting the immunization on the cattle; 2) screening for the serotype O foot-and-mouth disease virus antigen-specific single B cells; 3) amplifying variable region genes of the heavy and light chains; 4) acquiring constant region sequences of the heavy and light chains; 5) preparing a full-length heavy chain vector; 6) co-transfecting a cell, taking the supernatant of cell culture, and purifying. The method utilizes different foot-and-mouth disease virus strains to infect cattle and obtains a neutralizing antibody capable of neutralizing three topotypes of serotype O FMDVs by screening, and thus can obtain a whole bovine-derived broadly neutralizing monoclonal antibody.

7 Claims, 7 Drawing Sheets
Specification includes a Sequence Listing.

5-1             5-2

6-1             6-2

METHOD FOR PREPARING WHOLE BOVINE-DERIVED BROADLY NEUTRALIZING ANTIBODY AGAINST SEROTYPE O FOOT-AND-MOUTH DISEASE VIRUS

This application claims priority to Chinese application number 201810929067.1, filed Aug. 15, 2018, with a title of METHOD FOR PREPARING WHOLE BOVINE-DERIVED BROADLY NEUTRALIZING ANTIBODY AGAINST SEROTYPE O FOOT-AND-MOUTH DISEASE VIRUS. The above-mentioned patent application is incorporated herein by reference in its entirety.

TECHNICAL FIELD

The present invention relates to the technical field of antibody preparation, and in particular to a method for preparing a whole bovine-derived broadly neutralizing antibody against serotype O foot-and-mouth disease virus.

BACKGROUND

Foot-and-mouth disease (FMD) is a major animal epidemic disease that jeopardizes the healthy development of China's animal husbandry. It mainly affects artiodactyls such as cattle, sheep and pig, and has a significant impact on the international trade of livestock and its products. Foot-and-mouth disease virus (FMDV) is a small RNA virus that has quasispecies properties of an RNA virus. Also, FMDVs contain seven serotypes and have formed many genetic lineages with geographical features due to differences in epidemic regions, each of the serotype including multiple topotypes. There are currently 3 topotypes of serotype O FMDVs in China, which are respectively South-East Asia (SEA) (O/Mya98 lineage), Middle East-South Asia (ME-SA) (O/PanAsia lineage) and Cathay (an ancient and poetic name for China and east Tartary) (O/Cathay lineage). There are larger differences among antigenic structures of the three topotypes of viruses, and thus the cross immunoprotection effect is weak. The classic O/Cathay virus strain has relatively good immunogenicity and antigenic spectrum, but a newly isolated variant of it has a weakened immunogenicity and has a tendency of immune escape. Even for a virus strain with good immunogenicity, it also cannot provide good immunoprotection against a new epidemic virus strain that has a distant genetic relationship from this virus strain when the content of vaccine antigens is low; and it is necessary to develop a multi-component antigen vaccine to improve the antigenic spectrum of the vaccine. It is more difficult to screen for a vaccine virus strain with a broad antigenic spectrum, and it is necessary to construct an excellent vaccine virus strain by reversed genetics. Neutralizing antibodies are important components of FMD protective immunity, but there are still many gaps in the study of antigenic sites revealed by FMDV broadly neutralizing antibodies.

SUMMARY

An objective of the present invention is to provide a method for preparing a whole bovine-derived broadly neutralizing antibody against serotype O foot-and-mouth disease virus. The preparation method of the present invention utilizes different foot-and-mouth disease virus strains to infect cattle and obtains a neutralizing antibody capable of neutralizing three topotypes of serotype O FMDVs by screening, and thus can obtain a whole bovine-derived broadly neutralizing monoclonal antibody.

The present invention provides a method for preparing a whole bovine-derived broadly neutralizing antibody against serotype O foot-and-mouth disease virus, including the following steps:

1) conducting a first immunization on a cattle by using a serotype O foot-and-mouth disease virus, conducting a second immunization within 30-60 days after the first immunization, and conducting a third immunization within 120-150 days after the first immunization; where the serotype O foot-and-mouth disease viruses include the following three topotypes: a virus strain of South-East Asia topotype, a virus strain of Middle East-South Asia topotype, and a virus strain of Cathay topotype; and the serotype O foot-and-mouth disease viruses employed in the first immunization, the second immunization and the third immunization are of viruses from different topotypes;

2) after the third immunization, isolating a peripheral blood mononuclear cell, and screening for serotype O foot-and-mouth disease virus antigen-specific single B cells by using a bait antigen; where the bait antigen includes a serotype O foot-and-mouth disease virus labeled by biotin or a fluorescent protein;

3) using the cDNA of the serotype O foot-and-mouth disease virus antigen-specific single B cell obtained in step 2) as a template to amplify variable region genes of heavy and light chains of the bovine antibody;

4) using the total cDNA of the bovine peripheral blood mononuclear cell as a template to amplify the full-length sequences of the heavy and light chains of the bovine antibody, thereby obtaining constant region sequences of the heavy and light chains of the bovine antibody;

5) constructing the heavy chain variable region gene of the bovine antibody obtained in step 3) and the heavy chain constant region sequence of the bovine antibody obtained in step 4) into an expression vector to obtain a full-length heavy chain vector of the whole bovine-derived monoclonal antibody; and constructing the light chain variable region gene of the bovine antibody obtained in step 3) and the light chain constant region sequence of the bovine antibody obtained in step 4) into an expression vector to obtain a full-length light chain vector of the whole bovine-derived monoclonal antibody; and 6) mixing the full-length heavy chain vector of the whole bovine-derived monoclonal antibody and the full-length light chain vector of the whole bovine-derived monoclonal antibody obtained in step 5) at a mass ratio of 1:(1-3) to co-transfect a cell, taking a supernatant after culture of the transfected cells, and purifying to obtain a whole bovine-derived broadly neutralizing antibody against the serotype O foot-and-mouth disease virus; where there is no limitation in the order of steps 3) and 4).

Preferably, the virus strain of South-East Asia topotype as described in step 1) includes O/Mya98/JX/2010, O/GZ/CHA2010, O/BY/CHA/2010.

Preferably, the virus strain of Cathay topotype as described in step 1) includes O/HN/CHA/93, O/GD/China/86, O/YUN/TAW/97, O/XJ1/2003.

Preferably, the virus strain of Middle East-South Asia topotype as described in step 1) includes O/Tibet/99, O/YS/CHA/2005, O/TAW/2/99, O/CHA/7/2011.

Preferably, the fluorescent protein as described in step 2) includes FluoProbes 647H or Pacific Blue.

Preferably, the amplification of step 3) includes a nested PCR amplification method, and the primers used in the nested PCR amplification include: an IgG variable region outer primer pair, an IgG variable region inner primer pair, an IgM variable region outer primer pair, an IgM variable region inner primer pair, an IgD variable region outer primer pair, an IgD variable region inner primer pair, an Ig lambda outer primer pair, and an Ig lambda inner primer pair; where the upstream primer of each of the IgG variable region outer primer pair, the IgM variable region outer primer pair and the IgD variable region outer primer pair is identical and shown in SEQ ID NO.1, and the downstream primers of the IgG variable region outer primer pair, the IgM variable region outer primer pair and the IgD variable region outer primer pair are respectively shown in SEQ ID NO.2, SEQ ID NO.3 and SEQ ID NO.4; the upstream primer of each of the IgG variable region inner primer pair, the IgM variable region inner primer pair and the IgD variable region inner primer pair is identical and shown in SEQ ID NO.5, and the downstream primers of the IgG variable region inner primer pair, the IgM variable region inner primer pair and the IgD variable region inner primer pair are respectively shown in SEQ ID NO.6, SEQ ID NO.7 and SEQ ID NO.8; the nucleotide sequences of the Ig lambda outer primer pair are shown in SEQ ID NO.9 and SEQ ID NO.10; and the nucleotide sequences of the Ig lambda inner primer pair are shown in SEQ ID NO.11 and SEQ ID NO.12.

Preferably, the amplification of step 4) includes a method of rapid amplification of cDNA ends (RACEs), the primers used for the RACE includes: an IgG heavy chain 5'RACE primer with the nucleotide sequence shown in SEQ ID NO.13, an IgG heavy chain 3'RACE primer with the nucleotide sequence shown in SEQ ID NO.14, an IgG Lambda light chain 5'RACE primer with the nucleotide sequence shown in SEQ ID NO.15, an IgG Lambda light chain 3'RACE primer with the nucleotide sequence shown in SEQ. ID NO.16, an IgG Kappa light chain 5'RACE primer with the nucleotide sequence shown in SEQ ID NO.17, and an IgG Kappa light chain 3'RACE primer with the nucleotide sequence shown in SEQ ID NO.18.

Preferably, the bovine antibody described in steps 3) and 4) is an IgG antibody.

Preferably, the light chain described in steps 3) and 4) is a lambda light chain.

Preferably, the cell as described in step 6) includes a CHO-S cell.

The present invention provides a method for preparing a whole bovine-derived broadly neutralizing antibody against serotype O foot-and-mouth disease virus. The present invention utilizes a gene sequence of an existing bovine antibody for analyzing through homologous alignment, amplifies a variable region gene of the antibody from a single B lymphocyte and a constant region gene of the antibody from a peripheral blood mononuclear cell by nested PCR, thereby preparing a whole bovine-derived monoclonal antibody having a neutralizing antibody activity through screening. The present invention establishes for the first time a method for producing a whole bovine-derived monoclonal antibody by using a high-throughput single-B-cell technology, which has advantages such as having high efficiency, being entirely bovine-derived, and having good gene diversity as compared with a traditional antibody preparation technology. The propose of the present method provides a good method for studying the production of a broadly neutralizing antibody through induction by infecting cattle with serotype O foot-and-mouth disease viruses, and provides a new technical means for studying the antibody immune response of a cattle and isolating a therapeutic antibody.

DETAILED DESCRIPTION

Figure 1:
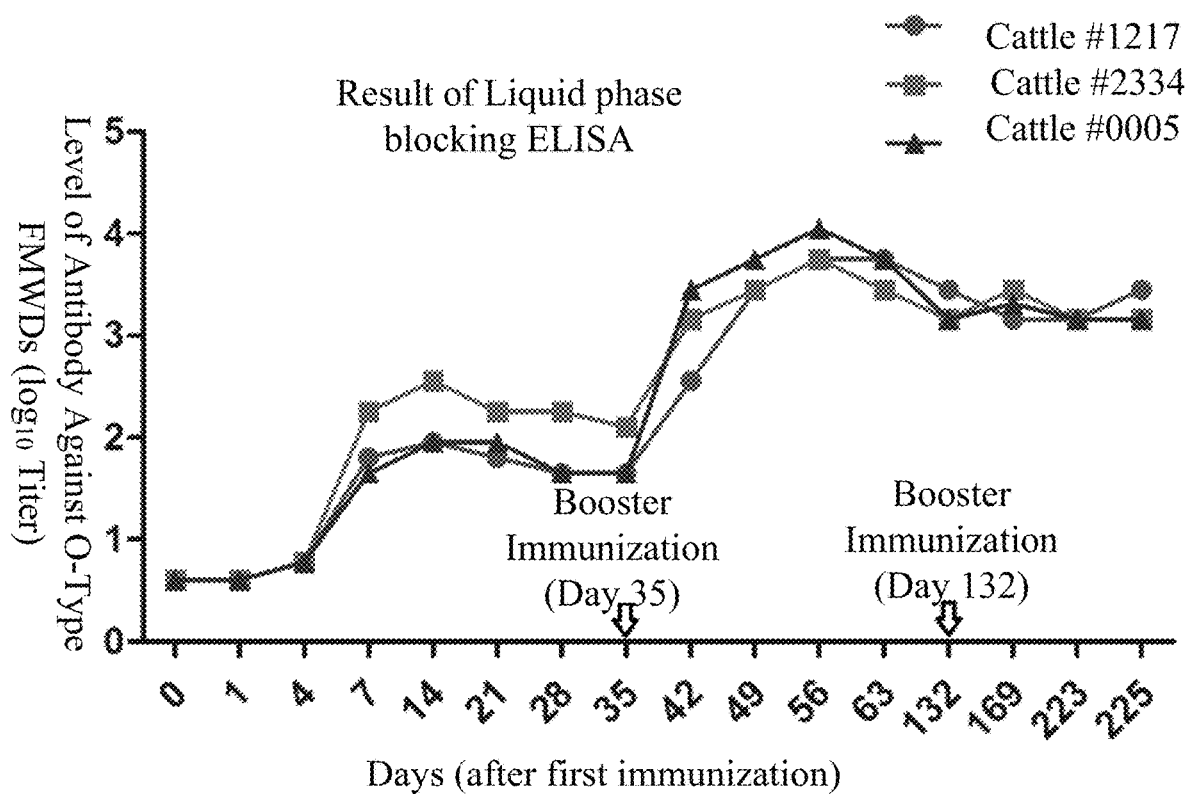
FIG. 1 is a curve of monitoring an antibody specific to serotype O FMDV as detected by liquid-phase blocking ELISA, as provided in Embodiment 1 of the present invention.

The present invention provides a method for preparing a whole bovine-derived broadly neutralizing antibody against serotype O foot-and-mouth disease virus, including the following steps:

1) conducting a first immunization on a cattle by using serotype O foot-and-mouth disease virus, conducting a second immunization within 30-60 days after the first immunization, and conducting a third immunization within 120-150 days after the first immunization; where the serotype O foot-and-mouth disease virus includes the following three topotypes: a virus strain of South-East Asia topotype, a virus strain of Cathay topotype, and a virus strain of Middle East-South Asia topotype; and the serotype O foot-and-mouth disease viruses employed in the first immunization, the second immunization and the third immunization are of different topotypes;

2) after the third immunization, isolating a peripheral blood mononuclear cell, and screening for serotype O foot-and-mouth disease virus antigen-specific single B cells by using a bait antigen; where the bait antigen includes serotype O foot-and-mouth disease virus labeled by biotin or a fluorescent protein;

3) using the cDNA of the serotype O foot-and-mouth disease virus antigen-specific single B cells obtained in step 2) as a template to amplify variable region genes of heavy and light chains of the bovine antibody;

4) using the total cDNA of the bovine peripheral blood mononuclear cell as a template to amplify the full-length sequences of the heavy and light chains of the bovine antibody, thereby obtaining constant region sequences of the heavy and light chains of the bovine antibody;

5) constructing the heavy chain variable region gene of the bovine antibody obtained in step 3) and the heavy chain constant region sequence of the bovine antibody obtained in step 4) into an expression vector to obtain a full-length heavy chain vector of the whole bovine-derived monoclonal antibody; and constructing the light chain variable region gene of the bovine antibody obtained in step 3) and the light chain constant region sequence of the bovine antibody obtained in step 4) into an expression vector to obtain a full-length light chain vector of the whole bovine-derived monoclonal antibody; and 6) mixing the full-length heavy chain vector of the whole bovine-derived monoclonal antibody and the full-length light chain vector of the whole bovine-derived monoclonal antibody obtained in step 5) at a mass ratio of 1:(1-3) to co-transfect a cell, taking a supernatant after culture of the transfected cells, and purifying to obtain a whole bovine-derived broadly neutralizing antibody against the serotype O foot-and-mouth disease virus;

there is no limitation in the order of steps 3) and 4).

In the present invention, the first immunization is conducted on the cattle by using the serotype O foot-and-mouth disease virus, the second immunization is conducted within 30-60 days after the first immunization, and the third immunization is conducted within 120-150 days after the first immunization; where the serotype O foot-and-mouth disease virus includes the following three topotypes: a virus strain of South-East Asia topotype, a virus strain of Cathay topotype, and a virus strain of Middle East-South Asia topotype; and the serotype O foot-and-mouth disease viruses employed in the first immunization, the second immunization and the third immunization are of viruses from different topotypes. In the present invention, more preferably the second immunization is conducted at the 35th day after the first immunization, and more preferably the third immunization is conducted at the 132th day after the first immunization. The present invention has no specific limitation on the inoculation method and dosage of the first, second and third immunization, and conventional immunization methods and dosages well known to those skilled in the art may be employed. For example, the first immunization of the present invention is preferably carried out by subcutaneous inoculation in a lingual surface of a cattle, and more preferably 2 mL antigens of 10000 BID50 are inoculated; the second and third immunization are preferably performed by intramuscular injection at the neck, and more preferably 5 mL of antigens that are emulsified with an ISA201 adjuvant are inoculated. In the present invention, the virus strain of South-East Asia topotype includes O/Mya98/JX/2010, O/GZ/CHA2010, O/B Y/CHA/2010, and more preferably is O/Mya98/JX/2010. In the present invention, the virus strain of Cathay topotype includes O/HN/CHA/93, O/GD/China/86, O/YUN/TAW/97, O/XJ1/2003, and more preferably is O/HN/CHA/93. In the present invention, the virus strain of Middle East-South Asia topotype includes O/Tibet/99, O/YS/CHA/2005, O/TAW/2/99, O/CHA/7/2011, and more preferably is O/Tibet/99. In the present invention, after the third immunization the peripheral blood mononuclear cell is isolated, and the serotype O foot-and-mouth disease virus antigen-specific single B cells are screened by using the bait antigen; where the bait antigen includes the serotype O foot-and-mouth disease virus labeled by biotin or a fluorescent protein. The present invention has no specific limitation on the species of the serotype O foot-and-mouth disease virus corresponding to the bait antigen, and a conventional serotype O foot-and-mouth disease virus may be used, where the virus is preferably the virus strain of the topological type of Central and Southeast Asian, and more preferably the virus strain O/Mya98/JX/2010. In the present invention, preferably the peripheral blood mononuclear cell is isolated at the 3-5th day after the third immunization, and the serotype O foot-and-mouth disease virus antigen-specific single B cells are screened preferably by using a flow cytometer, and more preferably by using a model BD FACSAriaII flow sorter. In the present invention, the bait antigen is more preferably a biotin-labeled serotype O foot-and-mouth disease virus. The present invention has no specific limitation on the biotin, as long as a conventional biotin which is well known to those skilled in the art may be used, such as a long-chain biotin EZ-Link™ Sulfo-NHS-LC-Biotin, Life Technology, USA. The present invention has no specific limitation on the biotin labeling method, and a conventional biotin labeling method which is well known to those skilled in the art may be employed. After the biotin labeling is performed, the cells are preferably stained before being screened by a flow cytometer. The present invention has no specific limitation on the staining method, and a conventional cell staining method which is well known to those skilled in the art may be employed. In the present invention, the fluorescent protein includes FluoProbes 647H or Pacific Blue.

In the present invention, after the serotype O foot-and-mouth disease virus antigen-specific single B cells are obtained, the cDNA of the serotype O foot-and-mouth disease virus antigen-specific single B cells is used as a template to amplify the variable region genes of the heavy and light chains of the bovine antibody. In the present invention, preferably a nested PCR method is employed for amplifying the variable region genes. The present invention has no specific limitation on the method for preparing the cDNA of the serotype O foot-and-mouth disease virus antigen-specific single B cells, and a conventional cDNA extraction or synthesis method which is well known to those skilled in the art may be used. In the present invention, preferably the extraction of the total RNA is first conducted, and then the total RNA is reverse transcripted to obtain the cDNA. The present invention has no specific limitation on the specific reaction condition parameters, and conventional operating parameters used in a cDNA synthesis process that are well known to those skilled in the art may be employed. In the present invention, primers are preferably designed according to the variable region genes of the heavy and light chains of the bovine antibody. In the present invention, it is preferred to introduce a merging base in the primer according to the differences in sequence, and the upstream primers (outer primers) of the heavy and light chains of the bovine antibody of the present invention is preferably located in a signal peptide region, and the downstream primers (inner and outer primers) are preferably located in a CH1 region. The primers used in the nested PCR amplification of the present invention include: an IgG variable region outer primer pair, an IgG variable region inner primer pair, an IgM variable region outer primer pair, an IgM variable region inner primer pair, an IgD variable region outer primer pair, an IgD variable region inner primer pair, an Ig lambda outer primer pair, and an Ig lambda inner primer pair; where the upstream primer of each of the IgG variable region outer primer pair, the IgM variable region outer primer pair and the IgD variable region outer primer pair is identical and shown in SEQ ID NO.1, and the downstream primers of the IgG variable region outer primer pair, the IgM variable region outer primer pair and the IgD variable region outer primer pair are respectively shown in SEQ ID NO.2, SEQ ID NO.3 and SEQ ID NO.4; the upstream primer of each of the IgG variable region inner primer pair, the IgM variable region inner primer pair and the IgD variable region inner primer pair is identical and shown in SEQ ID NO.5, and the downstream primers of the IgG variable region inner primer pair, the IgM variable region inner primer pair and the IgD variable region inner primer pair are respectively shown in SEQ ID NO.6, SEQ ID NO.7 and SEQ ID NO.8; the nucleotide sequences of the Ig lambda outer primer pair are shown in SEQ ID NO.9 and SEQ ID NO.10; and the nucleotide sequences of the Ig lambda inner primer pair are shown in SEQ ID NO.11 and SEQ ID NO.12. In the present invention, the bovine antibody preferably includes IgG, IgM and IgD, and more preferably includes IgG. In the present invention, the light chain of the bovine antibody is preferably an Ig lambda light chain. When an IgG bovine antibody is selected, the resulting neutralizing antibody has more affinity and higher neutralizing activity.

In the present invention, the total cDNA of the bovine peripheral blood mononuclear cell is used as a template to amplify the full-length sequences of the heavy and light chains of the bovine antibody, thereby obtaining constant region sequences of the heavy and light chains of the bovine antibody. In the present invention, the bovine antibody is preferably an IgG antibody, and when the IgG bovine antibody is selected, the resulting neutralizing antibody has more affinity and higher neutralizing activity. In the present invention, the amplification preferably includes a method of rapid amplification of cDNA ends (RACEs), the primers used for the RACE includes: an IgG heavy chain 5'RACE primer with the nucleotide sequence shown in SEQ ID NO.13, an IgG heavy chain 3'RACE primer with the nucleotide sequence shown in SEQ ID NO.14, an IgG Lambda light chain 5'RACE primer with the nucleotide sequence shown in SEQ ID NO.15, an IgG Lambda light chain 3'RACE primer with the nucleotide sequence shown in SEQ. ID NO.16, an IgG Kappa light chain 5'RACE primer with the nucleotide sequence shown in SEQ ID NO.17, and an IgG Kappa light chain 3'RACE primer with the nucleotide sequence shown in SEQ ID NO.18. The primers of the present invention are preferably designed according to the sequences of the bovine IgG heavy chain, Ig lambda light chain and Ig kappa light chain as published by GenBank. In the present invention, fragments at the 5' terminus and 3' terminus of the cDNA can be obtained by employing the method of rapid amplification of cDNA ends, and then spliced according to the overlap region parts of the two fragments, thereby finally obtaining a full-length sequence of the IgG heavy chain, the Ig lambda light chain and the Ig kappa light chain. In the present invention, the light chain is preferably a lambda light chain. Specifically in the embodiments of the present invention, the present invention obtains a plurality of full-length molecules of the IgG heavy chains, the lambda light chains and the Ig kappa light chains, and in the present invention finally the constant regions of an IgG heavy chain clone H 5-17 and an Ig Lambda light chain clone L1-7 serve as the constant region sequences of the heavy and light chains of the bovine antibody, for subsequent construction of the expression vector. The present invention has no specific limitation on the specific operating condition parameters of the method of rapid amplification of cDNA ends, and conventional operating conditions for the method of rapid amplification of cDNA ends that are well known to those skilled in the art may be used.

In the present invention, after the variable region and constant region sequences of the heavy chain of the bovine antibody and the variable region and constant region sequences of the light chain of the bovine antibody are obtained, the heavy chain variable region gene of the bovine antibody and the heavy chain constant region sequence of the bovine antibody are constructed into an expression vector to obtain the full-length heavy chain vector of the whole bovine-derived monoclonal antibody; and the light chain variable region gene of the bovine antibody and the light chain constant region sequence of the bovine antibody are constructed into an expression vector to obtain a full-length light chain vector of the whole bovine-derived monoclonal antibody. The present invention has no specific limitation on the method for constructing the vector, and conventional methods for constructing a heavy chain expression vector and a light chain expression vector used in a process of synthesizing antibodies as well known to those skilled in the art may be used. For example, in the present invention, during the process of constructing the expression vectors, preferably the heavy chain constant region and the light chain constant region are first amplified onto an expression vector, and then a Kozak sequence (GCCACC) is introduced in front of the start codon of the variable region sequence according to the variable region sequences of the heavy and light chains, subjected to codon optimization, and inserted into the expression vectors containing the heavy chain constant region and the light chain constant region, respectively. In the present invention, the expression vector preferably includes pcDNA3.1 or pcDNA3.4.

In the present invention, after the full-length heavy chain vector of the whole bovine-derived monoclonal antibody and the full-length light chain vector of the whole bovine-derived monoclonal antibody are obtained, the full-length heavy chain vector of the whole bovine-derived monoclonal antibody and the full-length light chain vector of the whole bovine-derived monoclonal antibody are mixed at a mass ratio of 1:(1-3) to co-transfect a cell, and a supernatant is taken after culture of the transfected cells and purified to obtain a whole bovine-derived broadly neutralizing antibody against the serotype O foot-and-mouth disease virus. In the present invention, the cell preferably includes a CHO-S cell. In the present invention, the ratio of the total mass of the full-length heavy chain vector of the whole bovine-derived monoclonal antibody and the full-length light chain vector of the whole bovine-derived monoclonal antibody to the number of cells for transfection is preferably 30 μg:($1\times10^8$-$2\times10^8$). In the present invention, after the full-length heavy chain vector of the whole bovine-derived monoclonal antibody and the full-length light chain vector of the whole bovine-derived monoclonal antibody are obtained, it is preferred to firstly transfer the full-length heavy chain vector of the whole bovine-derived monoclonal antibody and the full-length light chain vector of the whole bovine-derived monoclonal antibody into *E. coli* competent cells, respectively, an endotoxin-free plasmid is obtained by using an endotoxin-free plasmid extraction kit, and then the endotoxin-free plasmid is transfected into the cells. The present invention has no specific limitation on the conditions for transfection, and conventional conditions for transfecting a cell with a vector that are well known to those skilled in the art may be employed.

The method for preparing the whole bovine-derived broadly neutralizing antibody against the serotype O footand-mouth disease virus according to the present invention is further described in detail below with reference to the specific Embodiments, and the technical solutions of the present invention include, but are not limited to, the following Embodiments.

Deposit information for certain virus strains herein is as follows: Southeast Asian topotype virus strain O/GZ/CHA2010 of Serotype O foot-and-mouth disease virus was deposited at the Lanzhou Veterinary Research Institute (No. 1, Xujiaping, Chengguan District, Lanzhou, Gansu Province, P.R. China 730046) in March 2010 under Accession No. OGZ20100301. Southeast Asian topotype virus strain O/BY/CHA/2010 of Serotype O foot-and-mouth disease virus was deposited at the Lanzhou Veterinary Research Institute (No. 1, Xujiaping, Chengguan District, Lanzhou, Gansu Province, P.R. China 730046) in March 2010 under Accession No. OBY20100301. China topotype virus strain O/HN/CHA/93 of Serotype O foot-and-mouth disease virus was deposited at the Lanzhou Veterinary Research Institute (No. 1, Xujiaping, Chengguan District, Lanzhou, Gansu Province, P.R. China 730046) in March 1993 under Accession No. OHN19930301. China topotype virus strain O/YUN/TAW/97 of Serotype O foot-and-mouth disease virus was deposited at the Lanzhou Veterinary Research Institute (No. 1, Xujiaping, Chengguan District, Lanzhou, Gansu Province, P.R. China 730046) in December 1997 under Accession No. OYUN19971001. Central and Southeast Asian topotype virus strain O/Tibet/99 of Serotype O foot-and-mouth disease virus was deposited at the Lanzhou Veterinary Research Institute (No. 1, Xujiaping, Chengguan District, Lanzhou, Gansu Province, P.R. China 730046) in December 1999 under Accession No. OTIBET19991001. Central and Southeast Asian topotype virus strain O/YS/CHA/2005 of Serotype O foot-and-mouth disease virus was deposited at the Lanzhou Veterinary Research Institute (No. 1, Xujiaping, Chengguan District, Lanzhou, Gansu Province, P.R. China 730046) in December 2005 under Accession No. OYS20051001. And, Central and Southeast Asian topotype virus strain O/TAW/2/99 of Serotype O foot-and-mouth disease virus was deposited at the Lanzhou Veterinary Research Institute (No. 1, Xujiaping, Chengguan District, Lanzhou, Gansu Province, P.R. China 730046) in June 1999 under Accession No. OTAW19990601.

Embodiment 1

Animal Immuning 3 healthy Qinchuan cattle of 1 year old were selected for the preparation of whole bovine-derived monoclonal antibodies, and were numbered as #2334, #1217 and #0005 respectively. The cattle used in the experiment were all raised in the Lanzhou Veterinary Research Biosafety Level 3 (P3) Laboratory of the Chinese Academy of Agricultural Sciences. For the first immunization, 2 ml of cattle-adaptive O/Mya98/JX/2010 FMDV (the South-East Asia topotype) containing 10000 BID50 were inoculated by subcutaneous inoculation in a lingual surface of a cattle; on the 35th day after the first immunization, 5 ml of O/HN/CHA/93 FMDV (the Cathay topotype) that was emulsified with an ISA201 adjuvant was inoculated by intramuscular injection at the neck for the second immunization; and then on the 132nd day after the first immunization, 5 ml of O/Tibet/99 FMDV (the Middle East-South Asia topotype) that was emulsified with the ISA201 adjuvant was inoculated in the same way for the third immunization. Blood samples were collected periodically every other week, serum was separated, and the variation principle of the antibody titer after the virus infection was detected by using serotype O liquid-phase blocking ELSIA. Peripheral blood mononuclear cells were isolated 3-5 days after the third immunization, and then O/Mya98/JX/2010 FMDV 146S antigen-specific single B cells were sorted by a flow cytometer (BD Aria II, Biosciences), for screening and preparation of the broadly neutralizing antibody against the serotype O FMDV.

Antibody Response Characteristics

The total anti-FMDV IgG antibody in serum at different time points after immunization was detected by using the serotype O liquid-phase blocking ELISA (LPB-ELISA) kit (Lanzhou Veterinary Research Institute, China). The specific operations were carried out with reference to the instructions of the kit. The curve of monitoring the serotype O FMDV-specific antibody as detected by liquid-phase blocking ELISA was shown in FIG. 1. All three cattle began to produce FMDV-specific antibodies on the 4th day after infection and the production reached a peak on the 14th day; after the second immunization on the 35th day, the antibody level was obviously increased rapidly and reached the maximum peak on the 56th day; and the third immunization was carried out on the 132th day, then the antibody level was increased slightly and then maintained at the titer at the time of the third immunization.

Embodiment 2

Isolation of Bovine Antigen-Specific IgG$^+$, IgM$^+$, IgD$^+$ single B Cells

Isolation of Bovine peripheral blood mononuclear cells

Peripheral blood mononuclear cells (PBMCs) were isolated from bovine peripheral blood by using a lymphocyte separation solution ($\rho=1.083$, Histopaque, Sigma-aldrich), and the specific method was as follows.

a) The lymphocyte separation solution was placed at room temperature for equilibrium, and 6 mL of the lymphocyte separation solution was added into each 15 mL centrifuge tube.

b) An anticoagulant-treated bovine EDTA blood was diluted with a PBS solution at a ratio of 1:1, and then 8 mL of the diluted whole blood was aspirated by a pipette and slowly added into the upper layer of the lymph separation solution. Attention was paid to prevent blood from mixing into the lymph separation solution.

c) The centrifuge tube was put into a centrifugal machine equipped with a horizontal rotor, with the raising speed of the centrifugal machine being set to 6, the descending speed of the centrifugal machine being set to 1, and the temperature being 25° C. Centrifugation was conducted at 1200×g for 30 min.

d) The centrifuge tube was gently taken out, the upper layer of liquid was discarded through a pasteur pipet, and the milky white layer was the peripheral blood mononuclear cells. The milky white layer of cells was aspirated into a centrifuge tube containing ½ volume of a cell sorting solution. Centrifugation was conducted at 600×g for 5 min.

e) The upper layer of liquid was discarded at one time, added with 2-3 mL of a red blood cell lysis solution to lyse at room temperature for 1-2 min, and then quickly added with the cell sorting solution at more than 10 times of the volume. Centrifugation was conducted at 250×g for 10 min.

f) The upper layer of liquid was discarded at one time, and the bottom layer of cells was washed twice with the cell sorting solution, and then centrifuged at 400×g for 5 min.

g) The upper layer of liquid is poured out at one time, pipetted up and down into single cells with a pipette, and counted automatically by using a Cytell™ Cell Imaging System (GE, Healthcare, USA).

Biotin Labeling of O/Mya98/JX/2010 FMDV 146S Antigens

O/Mya98/JX/2010 FMDV 146S antigens were labeled with long-chain biotin (EZ-Link™ Sulfo-NHS-LC-Biotin, Life Technology, USA). The specific operations were as follows:

a) Firstly, the O/Mya98/JX/2010 FMDV 146S antigens were replaced into a PBS buffer by using an ultrafiltration tube with a cut-off of 100 KDa. Centrifugation was conducted at 4000 rpm for 10 min.

b) 180 μL ultrapure water was added to 1 mg biotin to dilute the biotin to 10 mM. The biotin was added at the ratios of 1:32, 1:64 and 1:128 respectively, i.e. 1 μL, 2 μL and 4 μL of the biotin were added respectively.

c) Reaction was conducted on ice at 4° C. for 2 h.

d) The solution was replaced into an antigen storage buffer via the ultrafiltration tube.

e) The solution was added with an equal volume of 100% glycerol, and stored at −70° C.

Cell Staining a) $5\times10^6$ enriched B cells were resuspended in 200 μL of a liquid, added with biotin-labeled O/Mya98/JX/2010 FMDV 146S antigens (0.5 μg), 3 μL mouse anti-bovine CD21-RPE (Bio-Rad, USA) and 1 μL mouse anti-bovine IgM-FITC (Bio-Rad, USA), and reacted at 4° C. for 20 min. The same cells were taken and set as a minus-one control sample (FMDV 146S antigens with no addition of biotin labeling). At the same time, a single positive tube is set to adjust the compensation between FITC, PE and APC.

b) The cells were washed twice with the cell sorting solution (centrifuging at 400×g and 4° C. for 5 min).

c) The cells were suspended in 200 μL of a liquid again, added with 1 μL of mouse anti-biotin-APC secondary antibody (Miltenyi-Biotec, German), and reacted at 4° C. for 20 min.

d) The cells were washed once with the cell sorting solution (centrifuging at 400×g and 4° C. for 5 min).

e) The cells were resuspended into single cells in 500 μL of a liquid, placed on ice, protected from light, and were ready for being sorted on a machine.

Flow Sorting of O/Mya98/JX/2010 FMDV146S Specific Single B Cells

The O/Mya98/JX/2010 FMDV146S specific single B cells were sorted by using a BD FACSAria II flow sorter. The setting parameters of the instrument were: the nozzle size: 100 μm; the sorting mode: a single cell mode; a sorting speed: 8000 cells/sec; an amplitude: 20 psi; and an oscillating frequency: 30 kHz. A Sweat button was turn off after the aforementioned parameters were set and adjusted, and an Accudrop (Cat: 642412, BD, USA) delay microsphere was used to calculate the liquid delay time. Then the position of a 96-PCR well plate in a sorting chamber was adjusted until the sorted cells accurately fallen into the center of the well on the plate (adjustment could be conducted by setting a mode in which 60 cells were sorted per well by using a 96-well plate attached with a sealing film). After all of the aforementioned settings were completed, a full skirt 96-PCR plate containing 10 μL of a lysis solution was put into the sorting chamber, and loading was started.

Distribution Characteristics of Antigen-Specific B Cells in Peripheral Blood Mononuclear Cells (PBMCs)

Figure 2:
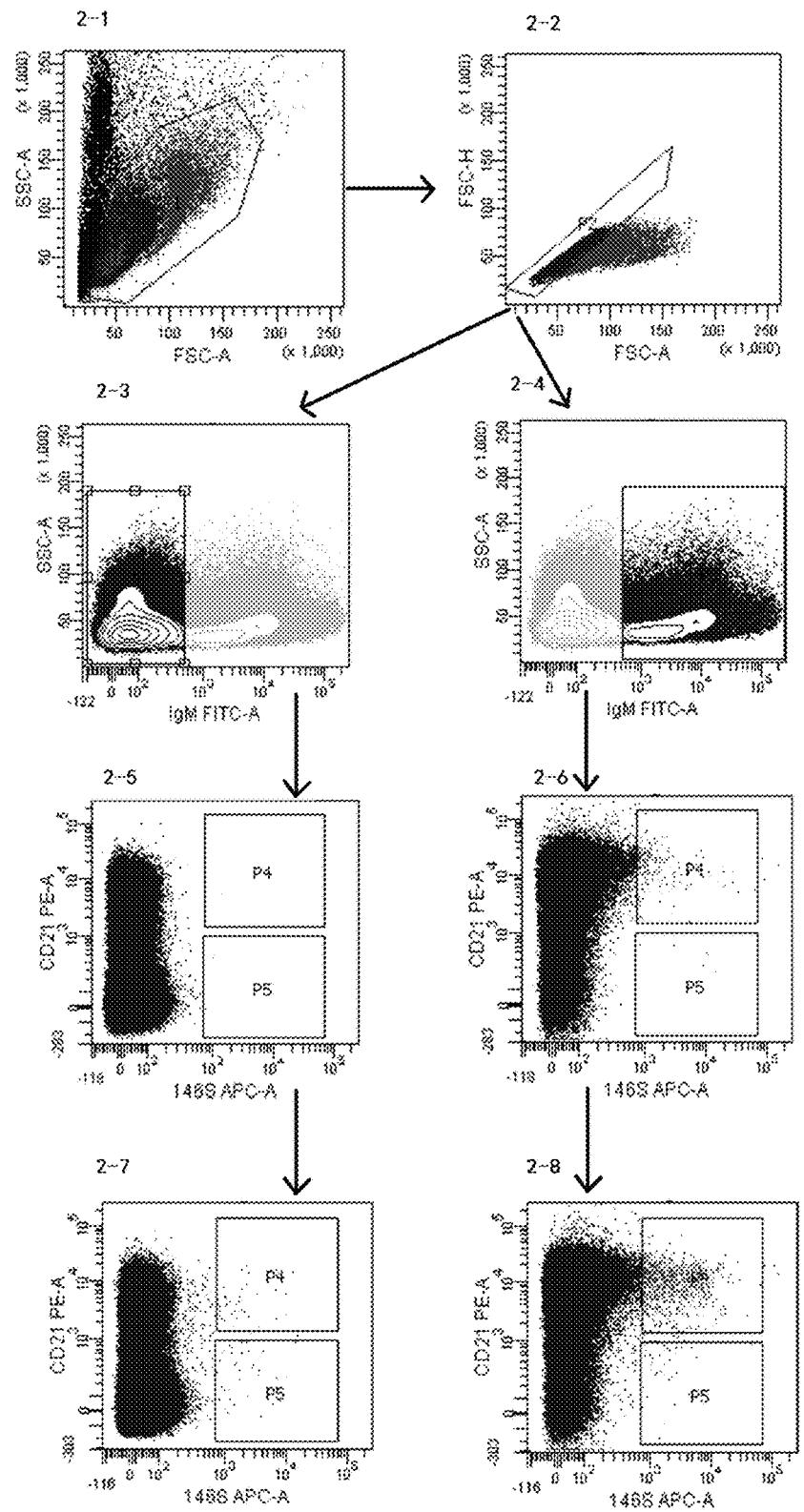
FIG. 2 is diagram showing a result of a multi-color flow cytometric analysis as provided in Embodiment 2 of the present invention.
Figure 3:
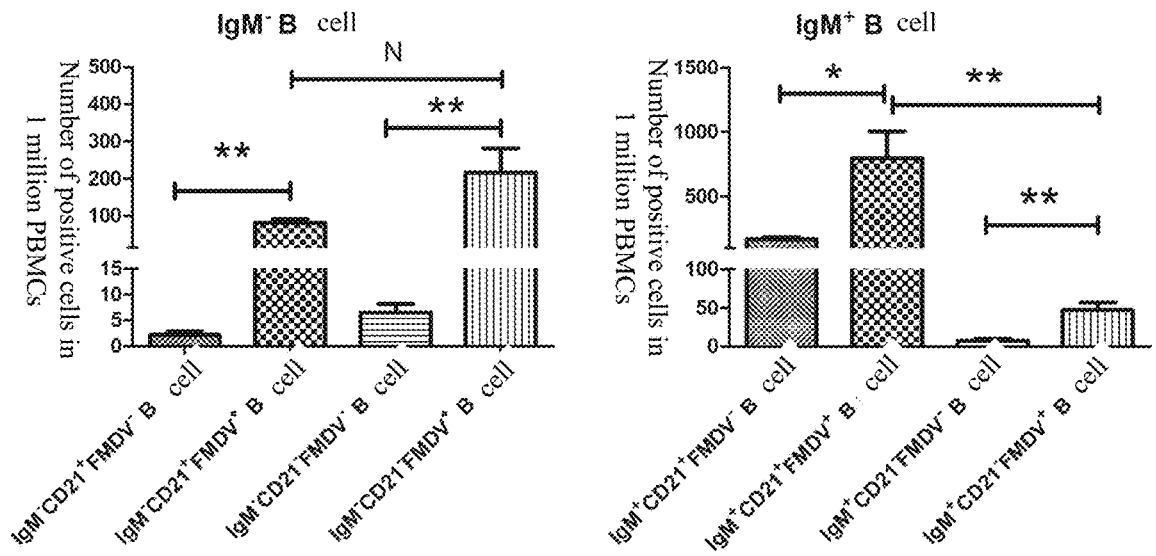
FIG. 3 is a diagram showing a result of the distribution of foot-and-mouth disease virus-specific B cells as provided in Embodiment 2 of the present invention.

The result of a multi-color flow cytometric analysis shown in FIG. 2 was that the FMDV specific B cells existed in populations of IgM$^-$ B cells and IgM$^+$ B cells. First PBMCs were circled by drawing a door (FIG. 2-1), adherent cells were excluded according to FSC-A and FSA-H settings, and single cells on a diagonal line were circled (FIG. 2-2). One million PBMCs were collected for analysis. In the population of IgM$^+$ cells (FIG. 2-4), the proportion of IgM$^+$ FMDV$^+$ B cells in PBMCs was about 0.83±0.2‰ (N=6, FIG. 2-8) as compared with a minus-one control sample (FIG. 2-6) (FMDV 146S antigens without addition of any biotin label); IgG$^+$ and IgD$^+$ B cells were included in the population of IgM$^-$ B cells (FIG. 2-3), where the proportion of IgM$^-$ FMDV$^+$ B cells in the peripheral blood mononuclear cells is about 0.30±0.15‰ (N=6, FIG. 2-7) as compared with the minus-one control sample (FIG. 2-5) (FMDV 146S antigens without addition of any biotin label) (the result of the distribution of foot-and-mouth disease virus-specific B cells was shown in FIG. 3, where FIG. 3-1 showed the distribution of the FMDV-specific B cells in each population of IgM$^-$ B cells, and FIG. 3-2 showed the distribution of FMDV-specific B cells in each population of IgM$^+$ B cells). CD21 was a marker molecule of mature B cells, and according to the distribution characteristics of CD21 (FIGS. 2-7 and 2-8), it could be seen that these FMDV-specific B cells included mature B cells and immature B cells. Therefore, CD21$^+$IgM$^+$FMDV$^+$ cells and CD21$^+$IgM$^-$FMDV$^+$ cells were finally selected to be sorted for subsequent PCR amplification of single B cells.

Embodiment 3

Preparation of Bovine Single B Cell Antibody

BCR Variable Region Gene Amplification of Bovine IgG$^+$, IgM$^+$, IgD$^+$ Single B Cells Design of Primers for BCR Variable Region Referring to the bovine IgG heavy chain, IgM heavy chain, IgD heavy chain sequences and Ig lambda light chain sequences published by GenBank, multiple sequence alignment was carried out, and a primer design software Primer 5.0 was used to design primers. The primers designed by the present invention were nested amplification primers, and merging bases were introduced into the primers according to sequence differences. An upstream primer was located in the signal peptide region, and the downstream primer was located in the CH1 region. The sequence of primers was shown in table 1.

TABLE 1

Nested Amplification Primers for Bovine IgG/IgM/IgD BCR Variable Region Gene

| Name of Primer | Sequence | Annealing Temperature (° C.) | Serial Number |
| --- | --- | --- | --- |
| IgG/IgM/IgD outer-F: | CCCTCCTCTTTGTGCTSTCAGCCC | 58/60 | SEQ ID NO. 1 |
| IgG outer-R: | GTCACCATGCTGCTGAGAGA | 60 | SEQ ID NO. 2 |
| IgM outer-R: | GGACCACCTGAGAGGAGGCCGAC | 58 | SEQ ID NO. 3 |
| IgD outer-R: | GTCCAGAATCTCTCGCTGCTGAC | 58 | SEQ ID NO. 4 |
| IgG/IgM/IgD inner-F: | AGAGGRGTYBTGTCCCAGG | 55 | SEQ ID NO. 5 |

TABLE 1-continued

Nested Amplification Primers for Bovine IgG/IgM/IgD BCR Variable Region Gene

| Name of Primer | Sequence | Annealing Temperature (° C.) | Serial Number |
|---|---|---|---|
| IgG inter-R: | CTTTCGGGGCTGTGGTGGAGGC | 55 | SEQ ID NO. 6 |
| IgM inner-R: | GGGGAAGGTCCAGAATCTCTCGC | 55 | SEQ ID NO. 7 |
| IgD inner-R: | ACGCAGGACACCAGGGGGAAGAC | 55 | SEQ ID NO. 8 |
| Ig lambda outer-F: | CACCATGGCCTGGTCCCCTCTG | 56 | SEQ ID NO. 9 |
| Ig lambda outer-R: | AAGTCGCTGATGAGACACACC | 56 | SEQ ID NO. 10 |
| Ig lambda inner-F: | TGGGCCCAGGCTGTRCTG | 55 | SEQ ID NO. 11 |
| Ig lambda inner-R: | GCGGGAACAGGGTGACCGAG | 55 | SEQ ID NO. 12 |

Preparation of Single-Cell cDNA Molecules

After the sorting was completed, 1 μL of a stop solution was added into 10 μL of a lysis solution in each well, reaction was conducted at room temperature for 5 min, and then the reaction was terminated. Then 4 μL of a SuperScriopt VIVO mix solution (Life Technology, USA) and 6 μL of DNase/RNase-free water were added into each well and mixed well. Centrifugation was conducted at 1500 rpm and 4° C. for 5 min. The cells were put into a 96-well PCR amplifier for reverse transcription amplification with the reaction conditions set as: at 25° C. for 10 min; at 42° C. for 120 min; at 85° C. for 5 min; and at 4° C. for 60 min. The cDNAs of the O/Mya98/JX/2010 FMDV 146S-specific single B cells were stored at −20° C. for subsequent PCR amplification.

Single-Cell PCR Amplification

By using the primers shown in Table 1, the BCR genes of the O/Mya98/JX/2010 FMDV 146S-specific single B cells were amplified by using a nested PCR method, where the BCR genes include the bovine IgG, IgM, and IgD heavy chain variable region genes, and the Ig lambda light chain variable region genes. The first round of reaction system was 25 μL, including 0.25 μL of a La Taq enzyme (Qiagen, German), 2.5 μL of 10×LA Taq Buffer II, 4 μL of a dNTP Mixture, 0.5 μL (10 μM) of an upstream/downstream primer, 14.75 μL of water, and 2.5 μL of a cDNA template. Reaction conditions: pre-denaturing at 95° C. for 5 min; denaturing at 95° C. for 30 s, annealing at 55° C./or 58° C./or 60° C. for 30 s, and extending at 72° C. for 1 min, with 35 cycles in total; and extending at 72° C. for another 10 min. Then, by taking 2.5 μL of the product of the first round as a template, a second round of amplification reaction was carried out referring to the aforementioned reaction system and according to the temperature conditions for annealing in Table 1.

Sequencing of PCR Products

5 μL of the PCR product of the second round of amplification was taken and subjected to electrophoresis on a 1.5% agarose gel to observe the amplification results. DNA sequencing was conducted on electrophoresis-positive samples by using a nested internal amplification primer, and the sequencing results were analyzed and aligned with DNASTAR software.

Results of BCR Amplification

By using the primers for amplifying IgM variable regions, the single $IgM^+$ $CD21^\pm$ B cells obtained through flow sorting were subjected to nested PCR amplification, the amplification products were subjected to electrophoresis and sequencing analysis, and IgM-expressing BCR genes were successful obtained (FIG. 4, where FIG. 4-1 showed the amplification result of the IgM heavy chain variable region, and FIG. 4-2 showed the amplification result of the IgM light chain variable region), where the heavy chain variable region fragment of the IgM-expressing BCR gene was about 380 bp and the light chain variable region fragment of it was about 350 bp. Multiple pairs of BCR genes of IgM were successfully amplified, verified by sequencing, and aligned with an IMGT database, confirming that the BCR gene with the sequence of IgM was obtained through amplification.

By using the primers for amplifying IgG and IgD variable regions, the single $IgM^-$ $CD21^\pm$ B cells obtained through flow sorting were subjected to nested PCR amplification, the amplification products were subjected to electrophoresis and sequencing analysis, and the BCR gene of IgG were successfully obtained through amplification (FIG. 5, where FIG. 5-1 showed the amplification result of the IgG heavy chain variable region, and FIG. 5-2 showed the amplification result of the IgG light chain variable region), where the heavy chain variable region fragment of the BCR gene was about 380 bp (information about all sequences of 330-510), and the light chain variable region fragment of the BCR gene was about 350 bp; and it was confirmed that the BCR gene with the sequence of IgG was obtained through amplification, as verified by sequencing and aligned with the IMGT database. The BCR gene of IgD was successfully obtained through amplification (FIG. 6, where FIG. 6-1 showed the amplification result of the IgD heavy chain variable region, and FIG. 6-2 showed the amplification result of the IgD light chain variable region), where the heavy chain variable region fragment of the BCR gene was between 350-500; and it was confirmed that the BCR gene with the sequence of IgD was obtained through amplification, as verified by sequencing and aligned with the IMGT database.

Full-Length Gene Amplification of Bovine IgG Molecular Heavy and Light Chains

An IgG molecule was a type of antibody that is dominant in the FMDV immune response, and was a source of high-affinity FDMV neutralizing antibodies. IgM and IgD were antibody molecules produced in the early stage of the immune response (3-7 days after the initial immunization). Such molecules have weak affinity and cannot be resistant to FMDV infection. After the booster (second) immunization, the immunoglobulin in the body was subjected to isotype switching to convert from IgM and IgD to IgG, and thus can be resistant to the FMDV infection. The present invention attempted to express bovine-derived FMDV-specific antibody molecules of IgM and IgD types, but these antibody molecules had poor affinity to FMDV and had no neutralizing activities. In view of this, antibody molecules of the IgG type were selected for preparation of the whole bovine-derived antibody.

Design of RACE Primers

Referring to sequences of the bovine IgG heavy chain, Ig lambda light chain and Ig kappa light chain published by GenBank, multiple sequence alignments were performed using the MEGA software to find a conserved region of a constant region, and then RACE primers for amplifying the bovine IgG heavy chain, Ig lambda light chain and Ig kappa light chain were designed in this region by using the primer design software Primer 5.0. The sequence of primers was shown in table 2.

TABLE 2

RACE Amplification Primers of Full-Length Genes of Heavy and Light Chains of Bovine IgG Molecules

| Name of Primer | Sequence | Annealing Temperature (° C.) | Serial Number |
| --- | --- | --- | --- |
| IgG heavy chain 5'RACE: | GATTACGCCAAGCTTCAGGACATACACC TGCGGCTCCCGGGC | 60 | SEQ ID NO. 13 |
| IgG heavy chain 3'RACE: | GATTACGCCAAGCTTCGAGCCGGTGACC GTGACCTGGAACTCG | 60 | SEQ ID NO. 14 |
| Lambda light chain 5'RACE: | GATTACGCCAAGCTTGCTCCCCTCGTGC GTGACCTCGCAGCTG | 60 | SEQ ID NO. 15 |
| Lambda light chain 3'RACE: | GATTACGCCAAGCTTCAGCAAGTACGYG GCCAGCAGCTAC | 60 | SEQ ID NO. 16 |
| Kappa light chain 5'RACE: | GATTACGCCAAGCTTCGAGGGTGGTAGT CAGGCTCTTGTGGC | 60 | SEQ ID NO. 17 |
| Kappa light chain 3'RACE: | GATTACGCCAAGCTTGAGCAGCTGAAGA CCGGAACTGTCTCTG | 60 | SEQ ID NO. 18 |

Extraction of Total RNA

The total RNA of the bovine peripheral blood mononuclear cells was extracted using an RNA extraction kit (Qiagen, German), and the specific steps were as follows:

a) $1 \times 10^6$ freshly isolated cell pellets were taken, added with 350 μL of RLT, vortexed, and allowed to stand for 3 min.

b) 350 μL of 75% ethanol was added, mixed well, and then transferred to a RNeasy Mini spin column, and centrifuged at 8000×g at room temperature for 15 s, and the flow-through liquid was discarded.

c) 350 μL of RW1 was added onto the column and centrifuged at 8000×g for 15 s at room temperature, and the flow-through liquid was discarded.

d) 80 μL of a DNase I working solution (10 μL of a DNase I stock solution and 70 μL of RDD) was added to the membrane at the bottom of the column, and static reaction was conducted at 20° C.-30° C. for 15 min.

e) The step 3 was repeated.

f) 500 μL of RPE was added onto the column and centrifuged at 8000×g for 15 s at room temperature, and the flow-through liquid was discarded.

g) 500 μL of RPE was added onto the column and centrifuged at 8000×g for 2 min at room temperature, and the flow-through liquid was discarded.

h) a new 2 mL collection tube was replaced, and centrifuged at 8000×g and at room temperature for 1 min when the tube was empty.

i) The centrifuged column was transferred to a new 1.5 mL collection tube, added with 35 μL of RNase-free water at the bottom of the column, and allowed to stand for 1 min.

j) Centrifugation was conducted at 8000×g and room temperature for 1 min. The eluate was collected for RNA quantification, and could be immediately transcribed into cDNA or stored at −70° C.

SMART RACE Amplification

The 5'-terminus and 3'-terminus gene sequences of bovine IgG heavy and light chains were amplified by the RACE method. The specific method was illustrated with reference to the instructions of a kit (SMARTer® RACE 5'/3' Kit, Takara, Japan), where firstly the 5'-RACE and 3'-RACE cDNA templates were obtained, and then subjected to RACE amplification by using gene-specific primers (GSPs). The specific method was as follows:

a) Preparation of 5'-RACE, 3'-RACE cDNA templates: firstly a mixture A (including 5 μL of 5×First-Strand Buffer, 0.5 μL of 100 mM DTT and 1 μL of dNTPs, and the reaction system can be scaled up) is prepared, centrifuged immediately after mixing, and allowed to stand at room temperature; then 5'-RACE ready cDNA (including 10 μL of the total RNA and 1 μL of a 5'-CDS primer A) and 3'-RACE ready cDNA (including 11 μL of the total RNA and 1 μL of a 3'-CDS primer A) mixtures are respectively prepared, mixed well, then reacted at 72° C. for 3 min, reacted at 42° C. for 2 min, centrifuged immediately after cooling, and the 5'-RACE ready cDNA sample was added with 1 μL of SMARTer II A Oligonucleotide, added q.s. to 12 μL, mixed well and then ready for use; meanwhile a mixture B (including 5.5 μL of the mixture A, 0.5 μL of a 40 U/μL RNase inhibitor and 2 μL of a 100 U SMARTScribe Reverse Transcriptase, and the reaction system can be scaled up) is prepared, and centrifuged immediately after mixing; and finally 8 μL of the prepared mixture B was added to the prepared 5'-RACE and 3'-RACE ready cDNAs, mixed well, centrifuged immediately after mixing, then reacted at 42° C. for 90 min, and then inactivated at 70° C. for 10 min. The obtained cDNA template was stored at −20° C.

b) RACE Amplification: By using the 5'-RACE and 3'-RACE cDNAs prepared above as templates, PCR amplification was carried out using the corresponding primers in Table 2. The reaction system included: 1 μL of SeqAmp DNA Polymerase, 2.5 μL of a template, 1 μL of a primer, 25 μL of a 2×SeqAmp buffer, 5 μL of 10×UPM, and 15.5 μL of H₂O, with the total volume being 50 μL. Reaction conditions: denaturing at 94° C. for 30 s, annealing at 68° C. for 30 s, and extending at 72° C. for 1 min, with 35 cycles in total. The reaction product was stored at −20° C.

Gene Cloning and Sequencing

First, the aforementioned PCR product was subjected to 1.5% agarose gel electrophoresis, and then purified according to the instructions of a DNA gel recovery kit to recover specific DNA bands. Referring to the operation steps stated in the instructions of pEASY®-T1 Cloning Kit (Beijing Full Gold, China) instructions for the procedure, 4 μL of the gel recovery fragment was taken, added with 1 μL of a pEASY®-T1 Cloning Vector, gently mixed, reacted at room temperature (20° C.-37° C.) for 5 min, and the centrifuge tube was placed on ice after the reaction was completed. Transformation of the ligation product was carried out according to the transformation operation instructions for TaKaRa DH5α Competent Cells. First, 5 μL of the ligation product was taken and added into 50 μL of DH5α competent cells, gently mixed and subjected to ice bath for 30 min; allowed to stand at 42° C. for 90 s, then immediately subjected to ice bath for 1-2 min; then added into a 950 μL antibiotic-free LB liquid medium, shaken gently (150-210 rpm) at 37° C. for 1 h; centrifuged at 400×g for 5 min; sterilized and the supernatant was discarded, and the cells were resuspended in 100 μL of the LB liquid medium; first 42 μL of X-gal (20 mg/mL) and 42 μL of IPTG (20 mg/mL) were uniformly applied onto an LB solid culture plate containing Amp (100 μg/mL), allowed to stand at 37° C. for 30 min for cellular attachment, then the resuspension solution was added by uniformly applying; and the coated petri dish was allowed to stand in a 37° C. incubator for culturing while facing upward for 30 min, and then culturing while facing downward for 12-16 h.

Several white colonies grown on the LB solid culture plate were randomly picked, respectively inoculated in a LB liquid medium containing Amp, and subjected to shake culture at 37° C. for 16 h. 5 ml of the bacterial solution was taken to extract plasmids, and DNA sequencing was carried out by using a M13 universal primer.

Full-Length Molecule Splicing of the IgG Molecular Heavy and Light Chains

The sequencing results were analyzed by DNAStar software. Firstly, the 5'-terminus and 3'-terminus sequences of the IgG heavy or light chain were subjected to homologous alignment by a ClustalW method in a MegAlign program, and then phylogenetic trees were established respectively. According to the results of phylogenetic trees, the 5'-terminus and 3'-terminus sequences located on the same branch belonged to the same heavy or light chain sequence. Then the 5'-terminus and 3'-terminus sequences located on the same branch were spliced by using DNAMAN molecular software, so as to obtain complete cDNA sequences of the complete IgG heavy chain, Ig kappa light chain, and Ig lambda light chain.

Acquisition of Full-Length Gene of Bovine IgG Molecular Heavy and Light Chains

Figure 7:
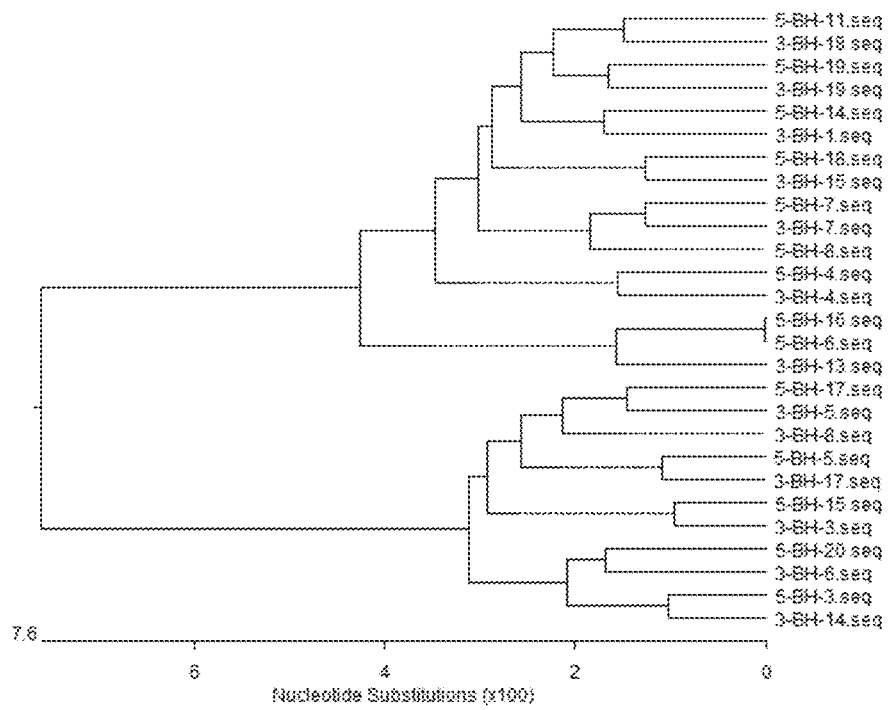
FIG. 7 is a phylogenetic analysis diagram of an IgG heavy chain sequence as provided in Embodiment 3 of the present invention.

Total RNA was extracted from bovine peripheral blood mononuclear cells, subjected to RACE amplification by using the IgG heavy chain 5'RACE primer and the IgG heavy chain 3'RACE primer in Table 2. subjected to sequencing, and aligned with the IMGT database to obtain 13 5-terminus sequences of IgG heavy chain (5-BH-11, 5-BH-19, 5-BH-14, 5-BH-18, 5-BH-16, 5-BH-4, 5-BH-7, 5-BH-8, 5-BH-17, 5-BH-5, 5-BH-15, 5-BH-20, 5-BH-3) and 12 3-terminus sequences of IgG heavy chain (3-BH-18, 3-BH-13, 3-BH-4, 3-BH-7, 3-BH-1, 3-BH-15, 3-BH-19, 3-BH-3, 3-BH-17, 3-BH-5, 3-BH-6, 3-BH-14). The aforementioned sequences were subjected to phylogenetic analysis (as shown in FIG. 7), and spliced to obtain 12 full-length sequences of the IgG heavy chain, which being H11-18, H19-19, H14-1, H18-15, H7-7, H4-4, H6-13, H17-5, H5-17, H15-3, H20-6, H3-14, respectively.

Figure 8:
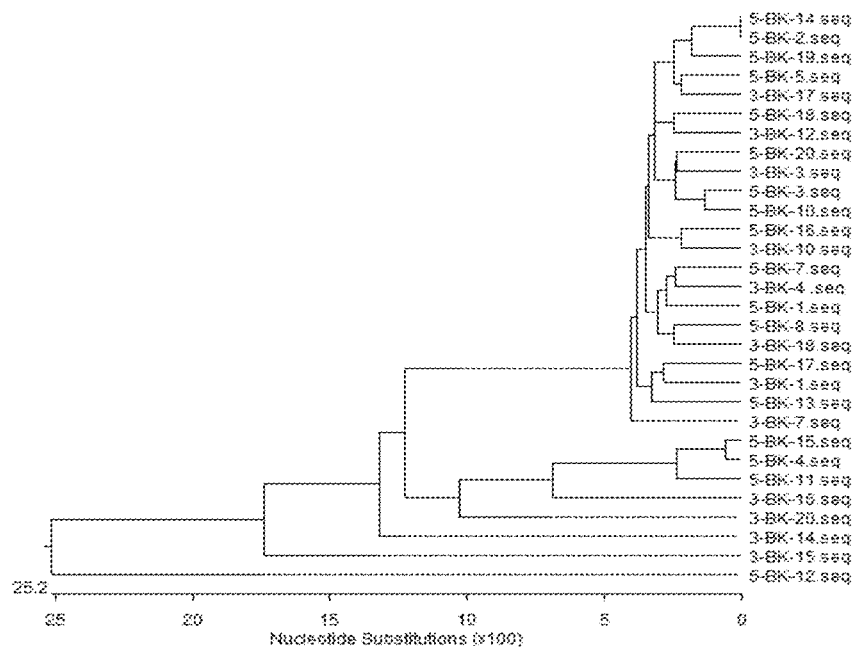
FIG. 8 is a phylogenetic analysis diagram of a Kappa light chain sequence as provided in Embodiment 3 of the present invention.

By using the 5'RACE and 3'RACE primers of the Kappa light chain as listed in Table 2, RACE amplification was conducted, and the product was subjected to sequencing and aligned with the IMGT database to successfully obtain 18 5-terminus sequences of the Kappa light chain (5-BK-14, 5-BK-2, 5-BK-19, 5-BK-5, 5-BK-18, 5-BK-20, 5-BK-3, 5-BK-10, 5-BK-16, 5-BK-7, 5-BK-1, 5-BK-8, 5-BK-17, 5-BK-13, 5-BK-15, 5-BK-4, 5-BK-11, 5-BK-12) and 12 3-terminus sequences of the Kappa light chain (3-BK-17, 3-BK-12, 3-BK-3, 3-BK-10, 3-BK-4, 3-BK-18, 3-BK-1, 3-BK-7, 3-BK-16, 3-BK-20, 3-BK-14, 3-BK-15). The aforementioned sequences were subjected to phylogenetic analysis (as shown in FIG. 8) and spliced to obtain multiple full-length sequences of the Kappa light chain, which were respectively K5-17, K7-4, K8-18, K16-10, K17-1, K18-12, K20-3.

Figure 9:
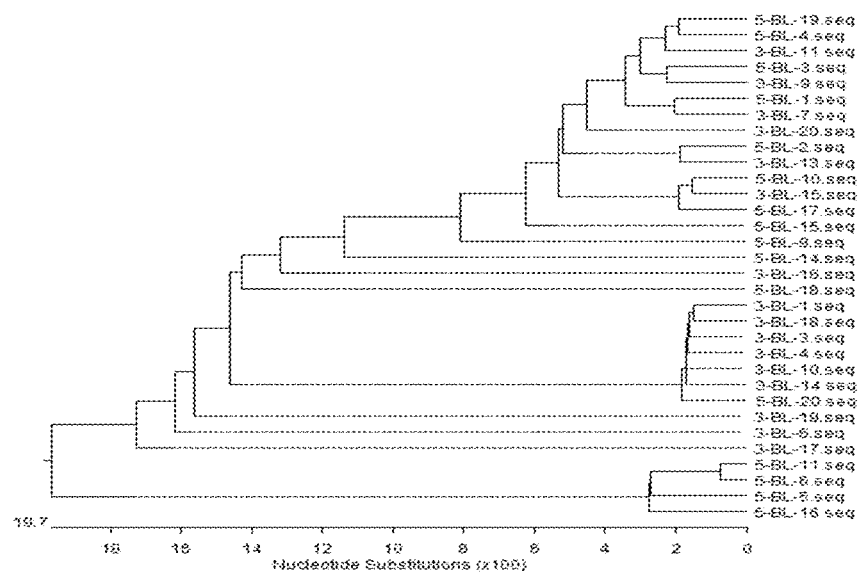
FIG. 9 is a phylogenetic analysis diagram of a Lambda light chain sequence as provided in Embodiment 3 of the present invention.

By using the 5'RACE and 3'RACE primers of the Lambda light chain as listed in Table 2, RACE amplification was conducted, and the product was subjected to sequencing and aligned with the IMGT database to obtain 16 5-terminus sequences of the Lambda light chain (5-BL-19, 5-BL-4, 5-BL-3, 5-BL-1, 5-BL-2, 5-BL-10, 5-BL-17, 5-BL-15, 5-BL-9, 5-BL-14, 5-BL-18, 5-BL-20, 5-BL-11, 5-BL-6, 5-BL-5, 5-BL-16) and 16 3-terminus sequences of the Lambda light chain (3-BL-11, 3-BL-9, 3-BL-7, 3-BL-20, 3-BL-13, 3-BL-15, 3-BL-16, 3-BL-1, 3-BL-18, 3-BL-3, 3-BL-4, 3-BL-10, 3-BL-14, 3-BL-19, 3-BL-6, 3-BL-17). The aforementioned sequences were subjected to establishment of a phylogenetic tree (as shown in FIG. 9), and spliced to finally obtain multiple full-length sequences of the Lambda light chain, which were respectively L 1-7, L 2-13, L3-9, L 10-15.

According to the full-length sequences obtained above, the bovine IgG heavy chain H5-17 constant region was selected as a framework template to construct a whole bovine-derived IgG heavy chain expression vector, and the Lambda light chain L1-7 constant region was selected as a framework template to construct a whole bovine-derived IgG light chain expression vector. A phylogenetic tree was constructed by aligning with the reference IgG sequence of the IMGT database, which indicated that the whole bovine-derived IgG molecule expressed using the aforementioned framework template was of an IgG2 subtype.

Expression of Whole Bovine-Derived Monoclonal IgG Antibody

Vector Construction

First, the constant region (CH1+CH2+CH3) gene sequences of H 5-17 was cloned and used as a bovine-derived IgG heavy chain, and MYC and HIS labels were introduced into the sequences at the C-terminus thereof, and the sequences were subjected to CHO codon optimization and then inserted into a pcDNA3.4 vector to obtain CH-pcDNA3.4; and the constant region (CH1) gene sequence of L1-7 was cloned and used as a bovine-derived Ig Lambda light chain, and the MYC and HIS labels were also introduced into the sequence at the C-terminus thereof, and the sequence was subjected to CHO codon optimization and then inserted into a pcDNA3.4 vector to obtain CL-pcDNA3.4.

Then a Kozak sequence (GCCACC) was introduced before the start codon based on the heavy chain variable region and light chain variable region genes obtained by PCR of single B cells, and then after CHO codon optimization, the genes were inserted into the CH-pcDNA3.4 and CL-pcDNA3.4 vectors through a NotI/NheI restriction site and a NheI/AleI restriction site to finally obtain full-length heavy chain and light chain vectors for expressing the whole bovine-derived IgG molecule.

Preparation of Endotoxin-Free Plasmids

The full-length heavy chain and light chain vectors for the whole bovine-derived IgG molecule obtained above were transferred into DH5a competent cells according to a conventional method, monoclonal colonies were picked into 5 ml of a LB medium, cultured at 37° C. overnight, then transferred to 200 ml of a LB medium at a ratio of 1:50, and continually cultured for 16 h. The bacterial cells were collected by centrifuging at 8228×g for 3 min, and subjected to extraction of endotoxin-free plasmids referring to the instructions of an endotoxin-free plasmid large extraction kit (Tiangen Biotech (Beijing) Co., Ltd.). The specific operation steps were as follows.

a) The bacterial cells were collected by centrifugation, and the residual liquid was aspirated to dry as much as possible. Then, the cells were added with 8 ml of a solution P1 (which had been added with the RNase A) and vortexed, and the bacterial cell pellet was shaken thoroughly.

b) The centrifuge tube was added with 8 ml of P2 and then immediately flipped up and down gently for 6-8 times to react at room temperature for 5 min.

c) The centrifuge tube was added with 8 ml of P4 and then immediately flipped up and down gently for 6-8 times, until a white flocculent precipitate appeared in the solution. Then reaction was conducted at room temperature for 10 min. The solution was centrifuged at 8228×g for 10 min at room temperature to separate the white precipitate to the bottom of the tube. All of the solution was carefully poured into a filter CS 1, and filtered by slowly pushing a push handle, and the filtrate was collected in a clean 50 ml centrifuge tube.

d) The filtrate was added with isopropanol at a volume which was 0.3 times of that of the filtrate, mixed well by inverting up and down, then transferred into an adsorption column CP6, and centrifuged at room temperature and at 8228×g for 2 min, the waste liquid was discarded from the collection tube, and the adsorption column CP6 was put back into the collection tube.

e) The adsorption column CP6 was added with 10 ml of a rinsing solution PW (which had been added with anhydrous ethanol) and centrifuged at 8228×g for 2 min, the waste liquid was discarded from the collection tube, and the adsorption column was put back into the collection tube.

f) The step e was repeated.

g) The adsorption column CP6 was added with 3 ml of anhydrous ethanol and centrifuged at room temperature and at 8228×g for 2 min, and the waste liquid was discarded.

h) The adsorption column CP6 was put back into the collection tube and centrifuged at 8228×g for 5 min to remove the residual rinsing solution.

i) The adsorption column CP6 was placed in a clean 50 ml centrifuge tube, added with 1 ml of ddH$_2$O at the middle of the adsorption membrane, allowed to stand at room temperature for 5 min, and then centrifuged at room temperature and at 8228×g for 2 min. The eluate was collected and assayed for the plasmid concentration, and stored at −20° C. until use.

Co-Transfection of CHO-S Suspension Cells with Heavy and Light Chain Vectors of the Antibody Suspended cells CHO-S were cultured in a 37° C. constant-temperature incubator containing 8% $CO_2$, with the shaking amplitude diameter being 50 mm and the rotation speed being set to 225 revolutions/minute. On the day before transfection, the density of the CHO-S cells was adjusted to $3 \times 10^6$ cells/ml and continually cultured for 18 h, and then a preheated fresh medium was replaced and the cell density was adjusted to $6 \times 10^6$ cells/ml. For transfection, first 30 µg of a mixture of heavy chain plasmids and light chain plasmids (at a ratio of heavy to light chain of 1:2) and 80 µL of a transfection reagent ExpiFectamine™ CHO were taken and placed into a 1.5 ml EP tube, respectively, each added with OptiPRO™ SFM to dilute to 1000 µL, gently inverted up and down for 4-5 times, and allowed to stand for 2 min. The prepared plasmids and transfection reagent were then mixed, and gently inverted up and down for 4-5 times to form a complex, then the complex was slowly added into about $1.5 \times 10^8$ CHO-S cells while stirring, and it should be ensured that the addition of the mixture was completed within 5 min. After transfection, the CHO-S cells were placed into a 37° C. constant-temperature incubator to subject to suspension culture for 18 h, and then supplemented with 150 µL of an ExpiCHO™ Enhancer and 6 ml of an ExpiCHO™ feed, and continually cultured at 37° C. for 9 days. The cells were centrifuged at 5000×g for 30 min to collect the cell culture supernatant for subsequent purification of antibodies.

Antibody Purification

The supernatant sample of the antibody-expressing cells was filtered through a 0.22 µM filter prior to purification, and then purified for antibodies on an AKTA protein purification system by using a Protein G column (Protein G HP, GE Bioscience). The specific operation steps were as follows.

a) The Protein G column was first equilibrated by using 5 column volumes of ddH$_2$O and a binding buffer (20 mM sodium phosphate buffer, pH=7.0) sequentially.

b) The flow rate was adjusted to 0.5 mL/min, and the loading was started.

c) After the loading was completed, the flow rate was adjusted to 2 mL/min, and the column was rinsed with 5 column volumes of a binding buffer.

d) The proteins of interest were eluted with an elution buffer (0.1 M glycine, pH=2.7), and the eluted proteins was collected with a 2 ml EP tube, and each tube was added with 60 µL of Tris-HCL (pH=9.0) before sample collection to adjust the pH of the eluted protein.

e) The eluted protein was exchanged into a PBS buffer through dialysis. The cells were stored at −20° C. until use.

Embodiment 4

Identification and Screening of Antibody

SDS-PAGE Electrophoresis

The expressed bovine-derived IgG antibodies were analyzed by SDS-PAGE electrophoresis. The specific operation steps were as follows.

a) The antibody sample to be tested was divided into two aliquots, respectively added with a reductive 5×SDS-loading buffer (with DTT) and a non-reductive 5×SDS-loading buffer (without DTT), and heated at 95° C. for 5 min.

b) A piece of 12% pre-made gel was taken, and loaded into a protein electrophoresis tank after the lower sealing film of the gel was teared off, and added with a MOPS buffer to a specified scale.

c) 30 µL/well of samples were loaded, and subjected to electrophoresis at a constant voltage of 100 V for 1 h.

d) After the electrophoresis was completed, the gel block was taken out, placed into a Coomassie blue staining solution, and shaken gently to react for 30 min.

e) Decolorization was carried out using a decolorizing solution, and reaction under shaking was carried out for 15 min.

f) The decolorizing solution was replaced until the background of the gel block is clear, and the gel was imaged.

The antibody was purified by a Protein G column. The purified product was analyzed by a reductive SDS-PAGE, and the diagram showing the reductive SDS-PAGE result of the expressed whole bovine-derived antibody molecules was shown in FIG. 10, indicating that the whole bovine-derived IgG molecule was successfully expressed, where the heavy chain molecule had a size of about 63 kDa, and the light chain molecule had a size of about 32 kDa; the non-reductive SDS-PAGE result (the diagram showing the non-reductive SDS-PAGE result of the expressed whole bovine-derived antibody molecules) was shown in FIG. 11, the full-length IgG molecule was about 190 kDa, and multiple bands greater than 150 kDa occurred below this band of the full-length IgG molecule, such that it is speculated that the IgG had been subjected to different degrees of glycosylation modification during the CHO-S expression.

Indirect Immunofluorescence Assay (IFA)

In this study, by means of BHK21 cells infected with FMDV (the O/Mya98/JX/2010 virus strain), the reactivity of the expressed whole bovine-derived monoclonal antibody to the FMDV antigen was evaluated via IFA. The specific operation steps were as follows:

a) On one day before the experiment, a 34-well plate was inoculated with the BHK21 cells, and then inoculated with the serotype O FMDV when the cells were grown to a single layer, placed into a 37° C. cell culture incubator, and absorbed for 2 h, and then the viral supernatant was discarded.

b) The cells were then fixed with a prechilled solution of methanol:acetone (1:1), and allowed to react at room temperature for 20 min.

c) The cells were washed with PBS for three times, and added with the whole bovine-derived monoclonal antibody to be tested at a concentration of 1-10 μg/mL, and incubated at 37° C. for 1 h.

d) The cells were washed with PBS for 3 times, added with the mouse anti-HIS-TAG FITC fluorescent antibody (with dilution of 1:1000), and incubated at 37° C. for 30 min.

e) The cells were washed with PBS for 3 times, and then observed and imaged under a fluorescence microscope.

Figure 4:
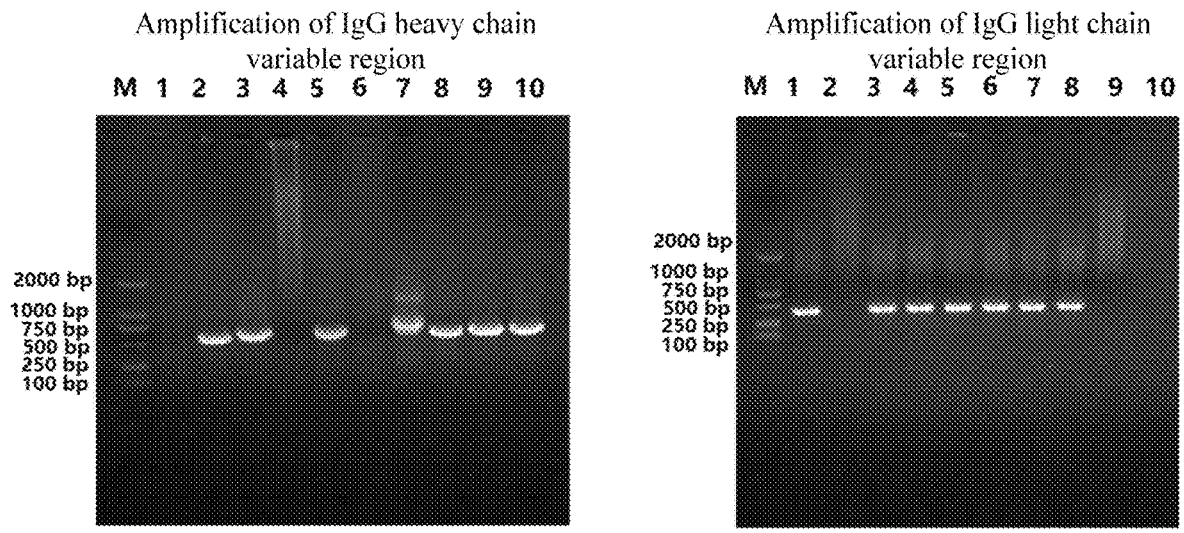
FIG. 4 is a diagram showing an electrophoresis result of a BCR gene for IgM as provided in Embodiment 3 of the present invention.
Figure 5:
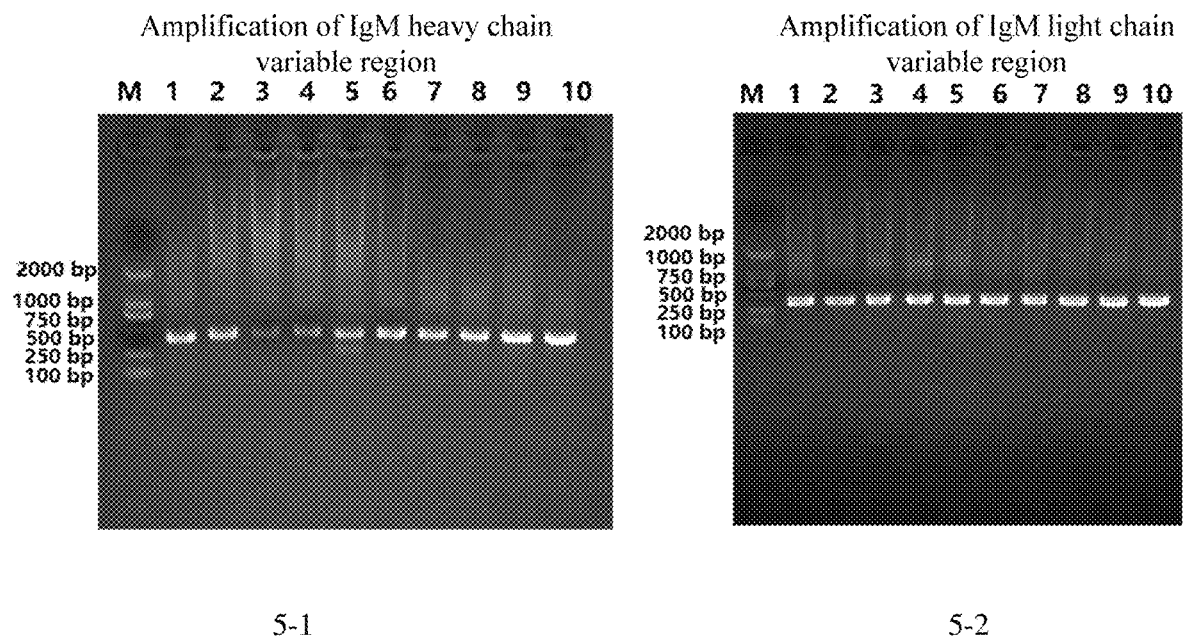
FIG. 5 is a diagram showing an electrophoresis result of a BCR gene for IgG as provided in Embodiment 3 of the present invention.
Figure 6:
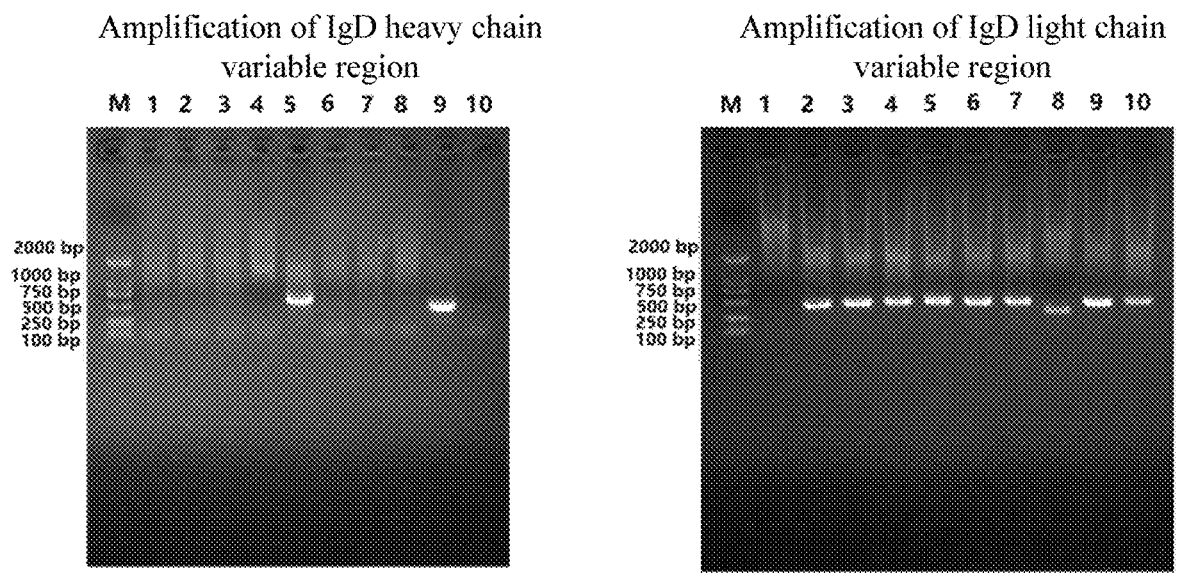
FIG. 6 is a diagram showing an electrophoresis result of a BCR gene for IgD as provided in Embodiment 3 of the present invention.
Figure 10:
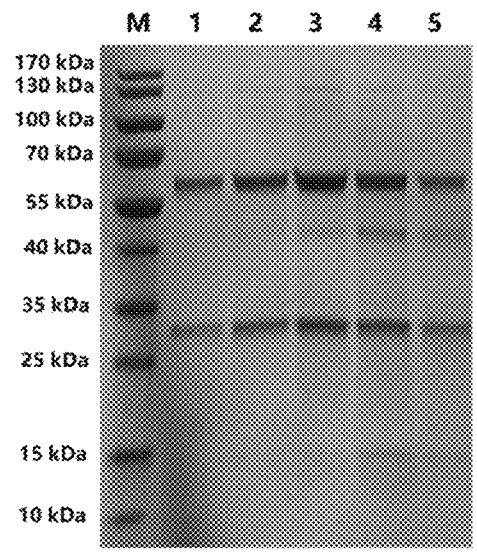
FIG. 10 is a diagram showing a reductive SDS-PAGE result of an expressed whole bovine-derived antibody molecule as provided in Embodiment 4 of the present invention.
Figure 11:
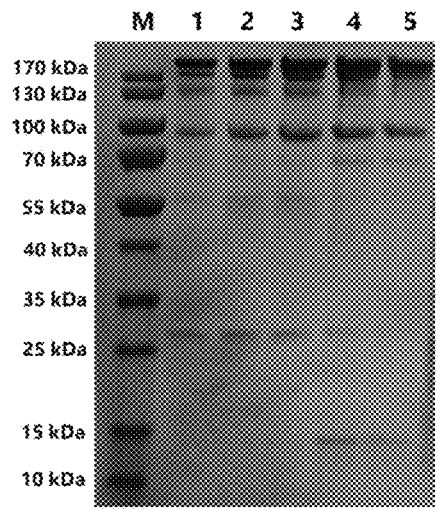
FIG. 11 is a diagram showing a non-reductive SDS-PAGE result of an expressed whole bovine-derived antibody molecule as provided in Embodiment 4 of the present invention.
Figure 12:
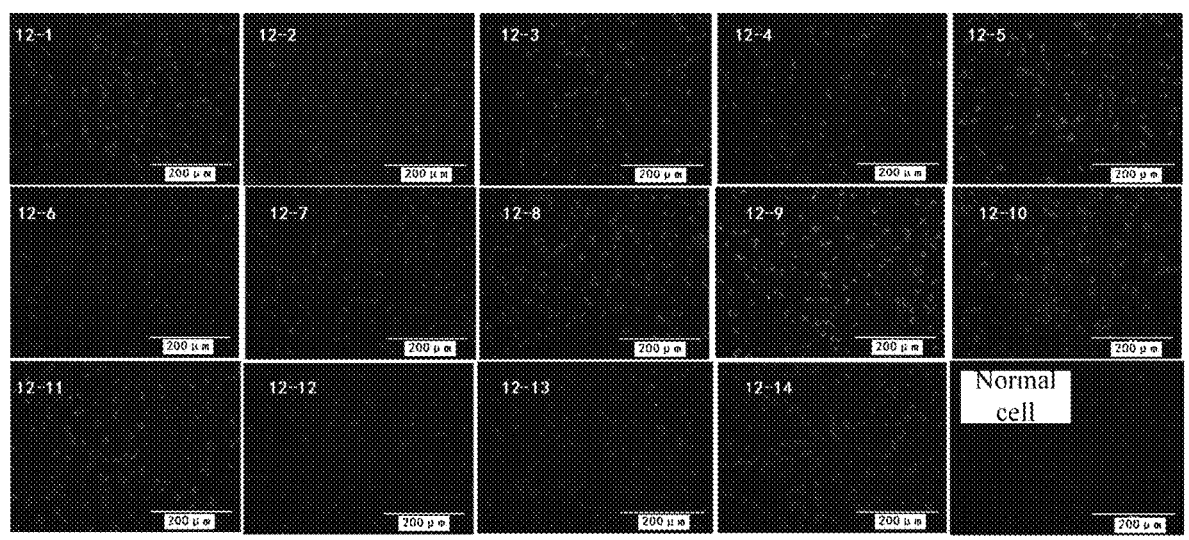
FIG. 12 is diagram showing an IFA result as provided in Embodiment 4 of the present invention.

The IFA results were shown in FIG. 12, where FIG. 12-1 showed the experiment results of the whole bovine-derived monoclonal antibody 1 and the BHK21 cells infected with the O/Mya98/JX/2010 virus strain; FIG. 12-2 showed the experiment results of the whole bovine-derived monoclonal antibody 2 and the BHK21 cells infected with the O/Mya98/JX/2010 virus strain; FIG. 12-3 showed the experiment results of the whole bovine-derived monoclonal antibody 3 and the BHK21 cells infected with the O/Mya98/JX/2010 virus strain; FIG. 12-4 showed the experiment results of the whole bovine-derived monoclonal antibody 4 and the BHK21 cells infected with the O/Mya98/JX/2010 virus strain; FIG. 12-5 showed the experiment results of the whole bovine-derived monoclonal antibody 5 and the BHK21 cells infected with the O/Mya98/JX/2010 virus strain; FIG. 12-6 showed the experiment results of the whole bovine-derived monoclonal antibody 6 and the BHK21 cells infected with the O/Mya98/JX/2010 virus strain; FIG. 12-7 showed the experiment results of the whole bovine-derived monoclonal antibody 7 and the BHK21 cells infected with the O/Mya98/JX/2010 virus strain; FIG. 12-8 showed the experiment results of the whole bovine-derived monoclonal antibody 8 and the BHK21 cells infected with the O/Mya98/JX/2010 virus strain; FIG. 12-9 showed the experiment results of the whole bovine-derived monoclonal antibody 9 and the BHK21 cells infected with the O/Mya98/JX/2010 virus strain; FIG. 12-10 showed the experiment results of the whole bovine-derived monoclonal antibody 10 and the BHK21 cells infected with the O/Mya98/JX/2010 virus strain; FIG. 12-11 showed the experiment results of the whole bovine-derived monoclonal antibody 11 and the BHK21 cells infected with the O/Mya98/JX/2010 virus strain; FIG. 12-12 showed the experiment results of the whole bovine-derived monoclonal antibody 12 and the BHK21 cells infected with the O/Mya98/JX/2010 virus strain; FIG. 12-13 showed the experiment results of the whole bovine-derived monoclonal antibody 13 and the BHK21 cells infected with the O/Mya98/JX/2010 virus strain; and FIG. 12-14 showed the experiment results of the whole bovine-derived monoclonal antibody 14 and the BHK21 cells infected with the O/Mya98/JX/2010 virus strain, and the negative control is normal BHK21 cells. The results showed that through screening, multiple strains of the expressed whole bovine-derived IgG molecules could specifically bind to the serotype O FMDV.

Virus Microneutralization Test

Three topotypes of serotype O FMDVs (O/Mya98/JX/2010, O/HN/CHA/93 and O/Tibet/99 virus strains) were used to conduct a virus cross-neutralization test on the immunized serum sample. The specific experimental steps were as follows:

a) 50 μL of the antibody to be tested was added into each well of a 96-well plate with serial dilution. Then, each well was added with 100 μL of the FMDV containing 100 $TCID_{50}$, and reacted at 37° C. for 1 h. Control wells containing 10, 100 and 1000 $TCID_{50}$ (without addition of serum samples) were also set.

b) Each well was added with 100 μL of a complete medium containing $5 \times 10^4$ BHK21 cells, and placed into a 37° C. incubator containing 5% $CO_2$ to react for 72 h.

c) The supernatant was discarded, and the cells were added with a prechilled stationary liquid (methanol:acetone=1:1) to fix at −20° C. for 20 min.

d) The stationary liquid was discarded, and each well was added with 100 μL of a crystal violet solution for staining. After 30 min, the 96-well plate was rinsed to observe the maximum dilution of a serum in which 50% of the cells were not diseased. Log 10 of the reciprocal of the maximum dilution of serum was used to represent the titer value of the virus neutralizing antibody (VNA).

Virus Neutralization Activity

Virus neutralization test results (Table 3) showed that among the expressed IgG molecules, the IgG molecules with serial numbers of 8, 10, 11, 12, 13 and 14 could neutralize three topotypes of serotype O FMDV viruses (the O/Mya98/JX/2010 virus strain, the O/HN/CHA/93 virus strain, and the O/Tibet/99 virus strain); the IgG molecules with serial numbers 2 and 5 could neutralize two topotypes of viruses (the O/Mya98/JX/2010 virus strain, and the O/HN/CHA/93 virus strain); the IgG molecules with the serial number 7 has a neutralization effect on the viruses of the Mya98 lingeage (the O/Mya98/JX/2010 virus strain)

TABLE 3

Neutralization Titers of Whole Bovine-Derived Monoclonal Antibodies to Three Topotypes of Serotype O FMDVs

| | FMDV neutralizing antibody | | |
|---|---|---|---|
| Serial Number | O/HN/CHA/93 | O/Tibet/99 | O/Mya98/JX/2010 |
| 1 | 1:4 | 1:4 | 1:4 |
| 2 | 1:128 | 1:8 | 1:256 |
| 3 | 1:4 | 1:4 | 1:4 |

TABLE 3-continued

Neutralization Titers of Whole Bovine-Derived Monoclonal Antibodies to Three Topotypes of Serotype O FMDVs

| Serial Number | FMDV neutralizing antibody | | |
|---|---|---|---|
| | O/HN/CHA/93 | O/Tibet/99 | O/Mya98/JX/2010 |
| 4 | 1:4 | 1:4 | 1:4 |
| 5 | 1:128 | 1:16 | 1:128 |
| 6 | 1:4 | 1:4 | 1:4 |
| 7 | 1:4 | 1:4 | 1:128 |
| 8 | 1:128 | 1:128 | 1:256 |
| 9 | 1:4 | 1:4 | 1:4 |
| 10 | 1:128 | 1:128 | 1:256 |
| 11 | 1:180 | 1:128 | 1:256 |
| 12 | 1:90 | 1:64 | 1:256 |
| 13 | 1:128 | 1:128 | 1:256 |
| 14 | 1:256 | 1:128 | 1:256 |

The above description is only a preferred embodiment of the present invention, and it should be noted that those skilled in the art can also make several improvements and retouchings without departing from the principles of the present invention. It should be considered as the scope of protection of the present invention.

What is claimed is:

1. A method for preparing a whole bovine-derived broadly neutralizing antibody against serotype O foot-and-mouth disease virus, comprising the following steps:
   1) conducting a first immunization on a cattle by using a serotype O foot-and-mouth disease virus, conducting a second immunization within 30-60 days after the first immunization, and conducting a third immunization within 120-150 days after the first immunization; wherein the Serotype O foot-and-mouth disease virus comprises the following three topotypes: a virus strain of South-East Asia topotype, a virus strain of Middle East-South Asia topotype, and a virus strain of Cathay topotype; and the serotype O foot-and-mouth disease viruses employed in the first immunization, the second immunization and the third immunization are of viruses from different topotypes;
   2) after the third immunization, isolating a peripheral blood mononuclear cell, and screening for serotype O foot-and-mouth disease virus antigen-specific single B cells by using a bait antigen; wherein the bait antigen comprises serotype O foot-and-mouth disease virus labeled by biotin or a fluorescent protein; and wherein the bait antigen is a 146S antigen;
   3) using the cDNA of the serotype O foot-and-mouth disease virus antigen-specific single B cell obtained in step 2) as a template to amplify variable region genes of heavy and light chains of the bovine antibody; wherein the amplification comprises a nested PCR amplification method, and the primers used in the nested PCR amplification comprise: an IgG variable region outer primer pair, an IgG variable region inner primer pair, an IgM variable region outer primer pair, an IgM variable region inner primer pair, an IgD variable region outer primer pair, an IgD variable region inner primer pair, an Ig lambda outer primer pair, and an Ig lambda inner primer pair; where the upstream primer of each of the IgG variable region outer primer pair, the IgM variable region outer primer pair and the IgD variable region outer primer pair are identical and have the sequence of SEQ ID NO. 1, and the downstream primers of the IgG variable region outer primer pair, the IgM variable region outer primer pair and the IgD variable region outer primer pair have the sequences of SEQ ID NO. 2, SEQ ID NO. 3 and SEQ ID NO. 4 respectively; the upstream primer of each of the IgG variable region inner primer pair, the IgM variable region inner primer pair and the IgD variable region inner primer pair are identical and have the sequence of SEQ ID NO. 5, and the downstream primers of the IgG variable region inner primer pair, the IgM variable region inner primer pair and the IgD variable region inner primer pair have the sequences of SEQ ID NO. 6, SEQ ID NO. 7 and SEQ ID NO. 8 respectively; the nucleotide sequences of the Ig lambda outer primer pair are the sequences of SEQ ID NO. 9 and SEQ ID NO. 10; and the nucleotide sequences of the Ig lambda inner primer pair are the sequences of SEQ ID NO. 11 and SEQ ID NO. 12;
   4) using the total cDNA of the bovine peripheral blood mononuclear cell as a template to amplify the full-length sequences of the heavy and light chains of the bovine antibody, thereby obtaining constant region sequences of the heavy and light chains of the bovine antibody; the amplification comprises a method of rapid amplification of cDNA ends, and the primers used for the rapid amplification of cDNA ends comprise: an IgG heavy chain 5' rapid amplification of cDNA end primer with the nucleotide sequence of SEQ ID NO. 13, an IgG heavy chain 3' rapid amplification of cDNA end primer with the nucleotide sequence of SEQ ID NO. 14, an IgG Lambda light chain 5' rapid amplification of cDNA end primer with the nucleotide sequence of SEQ ID NO. 15, an IgG Lambda light chain 3' rapid amplification of cDNA end primer with the nucleotide sequence of SEQ. ID NO. 16, an IgG Kappa light chain 5' rapid amplification of cDNA end primer with the nucleotide sequence of SEQ ID NO. 17, and an IgG Kappa light chain 3' rapid amplification of cDNA end primer with the nucleotide sequence of SEQ ID NO. 18;
   5) constructing the heavy chain variable region gene of the bovine antibody obtained in step 3) and the heavy chain constant region sequence of the bovine antibody obtained in step 4) into an expression vector to obtain a full-length heavy chain vector of the whole bovine-derived monoclonal antibody; and constructing the light chain variable region gene of the bovine antibody obtained in step 3) and the light chain constant region sequence of the bovine antibody obtained in step 4) into an expression vector to obtain a full-length light chain vector of the whole bovine-derived monoclonal antibody; and
   6) mixing the full-length heavy chain vector of the whole bovine-derived monoclonal antibody and the full-length light chain vector of the whole bovine-derived monoclonal antibody obtained in step 5) at a mass ratio of 1:(1-3) to co-transfect a cell, taking a supernatant after culture of the transfected cells, and purifying to obtain a whole bovine-derived broadly neutralizing antibody against the serotype O foot-and-mouth disease virus; wherein there is no limitation in the order of steps 3) and 4).

2. The preparation method according to claim 1, wherein the virus strain of the topological type of Southeast Asian as described in step 1) is chosen from O/GZ/CHA2010 and O/BY/CHA/2010.

3. The preparation method according to claim 1, wherein the virus strain of the topological type of China as described in step 1) is chosen from O/HN/CHA/93 and O/YUN/TAW/97.

4. The preparation method according to claim 1, wherein the virus strain of the topological type of Central and Southeast Asian as described in step 1) is chosen from O/Tibet/99, O/YS/CHA/2005, and O/TAW/2/99.

5. The preparation method according to claim 1, wherein the bovine antibody described in steps 3) and 4) is an IgG antibody.

6. The preparation method according to claim 1, wherein the light chain described in steps 3) and 4) is a lambda light chain.

7. The preparation method according to claim 1, wherein the cell as described in step 6) comprises a CHO-S cell.

* * * * *

SEQUENCE LISTING

```
<160> NUMBER OF SEQ ID NOS: 18

<210> SEQ ID NO 1
<211> LENGTH: 24
<212> TYPE: DNA
<213> ORGANISM: artificial sequence
<220> FEATURE:
<223> OTHER INFORMATION: IgG/IgM/IgD outer-F

<400> SEQUENCE: 1
ccctcctctt tgtgctstca gccc                                          24

<210> SEQ ID NO 2
<211> LENGTH: 20
<212> TYPE: DNA
<213> ORGANISM: artificial sequence
<220> FEATURE:
<223> OTHER INFORMATION: IgG outer-R

<400> SEQUENCE: 2
gtcaccatgc tgctgagaga                                               20

<210> SEQ ID NO 3
<211> LENGTH: 23
<212> TYPE: DNA
<213> ORGANISM: artificial sequence
<220> FEATURE:
<223> OTHER INFORMATION: IgM outer-R

<400> SEQUENCE: 3
ggaccacctg agaggaggcc gac                                           23

<210> SEQ ID NO 4
<211> LENGTH: 23
<212> TYPE: DNA
<213> ORGANISM: artificial sequence
<220> FEATURE:
<223> OTHER INFORMATION: IgD outer-R

<400> SEQUENCE: 4
gtccagaatc tctcgctgct gac                                           23

<210> SEQ ID NO 5
<211> LENGTH: 19
<212> TYPE: DNA
<213> ORGANISM: artificial sequence
<220> FEATURE:
<223> OTHER INFORMATION: IgG/IgM/IgD inner-F
```

```
<400> SEQUENCE: 5
agaggrgtyb tgtcccagg                                               19

<210> SEQ ID NO 6
<211> LENGTH: 22
<212> TYPE: DNA
<213> ORGANISM: artificial sequence
<220> FEATURE:
<223> OTHER INFORMATION: IgG inter-R

<400> SEQUENCE: 6
ctttcggggc tgtggtggag gc                                           22

<210> SEQ ID NO 7
<211> LENGTH: 23
<212> TYPE: DNA
<213> ORGANISM: artificial sequence
<220> FEATURE:
<223> OTHER INFORMATION: IgM inner-R

<400> SEQUENCE: 7
ggggaaggtc cagaatctct cgc                                          23

<210> SEQ ID NO 8
<211> LENGTH: 23
<212> TYPE: DNA
<213> ORGANISM: artificial sequence
<220> FEATURE:
<223> OTHER INFORMATION: IgD inner-R

<400> SEQUENCE: 8
acgcaggaca ccaggggggaa gac                                         23

<210> SEQ ID NO 9
<211> LENGTH: 22
<212> TYPE: DNA
<213> ORGANISM: artificial sequence
<220> FEATURE:
<223> OTHER INFORMATION: Ig lambda outer-F

<400> SEQUENCE: 9
caccatggcc tggtcccctc tg                                           22

<210> SEQ ID NO 10
<211> LENGTH: 21
<212> TYPE: DNA
<213> ORGANISM: artificial sequence
<220> FEATURE:
<223> OTHER INFORMATION: Ig lambda outer-R

<400> SEQUENCE: 10
aagtcgctga tgagacacac c                                            21

<210> SEQ ID NO 11
<211> LENGTH: 18
<212> TYPE: DNA
<213> ORGANISM: artificial sequence
<220> FEATURE:
<223> OTHER INFORMATION: Ig lambda inner-F

<400> SEQUENCE: 11
tgggcccagg ctgtrctg                                                18

<210> SEQ ID NO 12
```

```
<211> LENGTH: 20
<212> TYPE: DNA
<213> ORGANISM: artificial sequence
<220> FEATURE:
<223> OTHER INFORMATION: Ig lambda inner-R

<400> SEQUENCE: 12
gcgggaacag ggtgaccgag                                               20

<210> SEQ ID NO 13
<211> LENGTH: 42
<212> TYPE: DNA
<213> ORGANISM: artificial sequence
<220> FEATURE:
<223> OTHER INFORMATION: IgG heavy chain

<400> SEQUENCE: 13
gattacgcca agcttcagga catacacctg cggctcccgg gc                      42

<210> SEQ ID NO 14
<211> LENGTH: 43
<212> TYPE: DNA
<213> ORGANISM: artificial sequence
<220> FEATURE:
<223> OTHER INFORMATION: IgG heavy chain

<400> SEQUENCE: 14
gattacgcca agcttcgagc cggtgaccgt gacctggaac tcg                     43

<210> SEQ ID NO 15
<211> LENGTH: 43
<212> TYPE: DNA
<213> ORGANISM: artificial sequence
<220> FEATURE:
<223> OTHER INFORMATION: Lambda light chain

<400> SEQUENCE: 15
gattacgcca agcttgctcc cctcgtgcgt gacctcgcag ctg                     43

<210> SEQ ID NO 16
<211> LENGTH: 40
<212> TYPE: DNA
<213> ORGANISM: artificial sequence
<220> FEATURE:
<223> OTHER INFORMATION: Lambda light chain

<400> SEQUENCE: 16
gattacgcca agcttcagca agtacgyggc cagcagctac                         40

<210> SEQ ID NO 17
<211> LENGTH: 42
<212> TYPE: DNA
<213> ORGANISM: artificial sequence
<220> FEATURE:
<223> OTHER INFORMATION: Kappa light chain

<400> SEQUENCE: 17
gattacgcca agcttcgagg gtggtagtca ggctcttgtg gc                      42

<210> SEQ ID NO 18
<211> LENGTH: 43
<212> TYPE: DNA
<213> ORGANISM: artificial sequence
```

```
<220> FEATURE:
<223> OTHER INFORMATION: Kappa light chain

<400> SEQUENCE: 18
gattacgcca agcttgagca gctgaagacc ggaactgtct ctg                              43
```